United States Patent [19]

Murayama et al.

[11] Patent Number: 5,831,000
[45] Date of Patent: Nov. 3, 1998

[54] HYBRID CALCITONIN

[75] Inventors: Eigoro Murayama, Shizuoka-ken; Tohru Hoshi, Kanagawa-ken, both of Japan

[73] Assignees: Chugai Seiyaku Kabushiki Kaisha; Asahi Glass Co., Ltd., both of Tokyo, Japan

[21] Appl. No.: 322,386

[22] Filed: Oct. 12, 1994

Related U.S. Application Data

[63] Continuation of Ser. No. 941,072, Oct. 9, 1992, abandoned.

[30] Foreign Application Priority Data

Apr. 9, 1990 [JP] Japan ................................ 2-93656
Sep. 1, 1990 [JP] Japan ................................ 2-231913

[51] Int. Cl.[6] ................................................. A61K 14/585
[52] U.S. Cl. ................... 530/307; 530/317; 530/324; 514/11; 930/60
[58] Field of Search ........................ 530/307, 317, 530/324; 514/11; 930/60

[56] References Cited

U.S. PATENT DOCUMENTS

| Re. 32,347 | 2/1987 | Neher et al. | 530/307 |
|---|---|---|---|
| 3,798,203 | 3/1974 | Brugger et al. | 530/307 |
| 3,910,872 | 10/1975 | Riniker et al. | 530/307 |
| 4,086,221 | 4/1978 | Sakakibara et al. | 530/307 |
| 4,605,515 | 8/1986 | Orlowski et al. | 530/307 |
| 4,658,014 | 4/1987 | Kempe | 530/307 |
| 4,732,969 | 3/1988 | Orlowski et al. | 530/307 |
| 4,758,550 | 7/1988 | Cardinaux et al. | 530/307 |

FOREIGN PATENT DOCUMENTS

| 1950711 | 4/1970 | Germany . |
|---|---|---|
| 8500165 | 1/1985 | WIPO . |

OTHER PUBLICATIONS

Murayama et al, Chem. Abs. 116, No. 106,823 (Equivalent to PCT Int'l. Appl 15,)511, 1991.

Rene Maier et al, "Analogs of human calcitonin, I. Influence of modifications in amino acid positions 29 and 31 on hypocalcaemic activity in the rat," *FEBS Letters*, vol. 48, No. 1, pp. 68–71, (1974).

R. Maier, "Analogues of Human Cacitonin," *Calcitonin Tissue Research*, vol. 21, Suppl., pp. 317–320, (1976).

*Primary Examiner*—Ponnathapura Achutamurthy
*Assistant Examiner*—T. D. Wessendorf
*Attorney, Agent, or Firm*—Browdy and Neimark

[57] ABSTRACT

The improved hybrid calcitonin has a peptide segment in human calcitonin and a peptide segment in calcitonin derived from animals other than humans, such as eel, salmon and chicken. Each of the human or human analog calcitonins and the calcitonins derived from animals other than humans may be either native calcitonin or an analog thereof. The hybrid calcitonin has the outstanding advantage that it exhibits biological activities as strong as eel, salmon and chicken calcitonin while causing no side effects including nausea, disorders in the functions of the digestive tract or antigenicity.

7 Claims, 9 Drawing Sheets

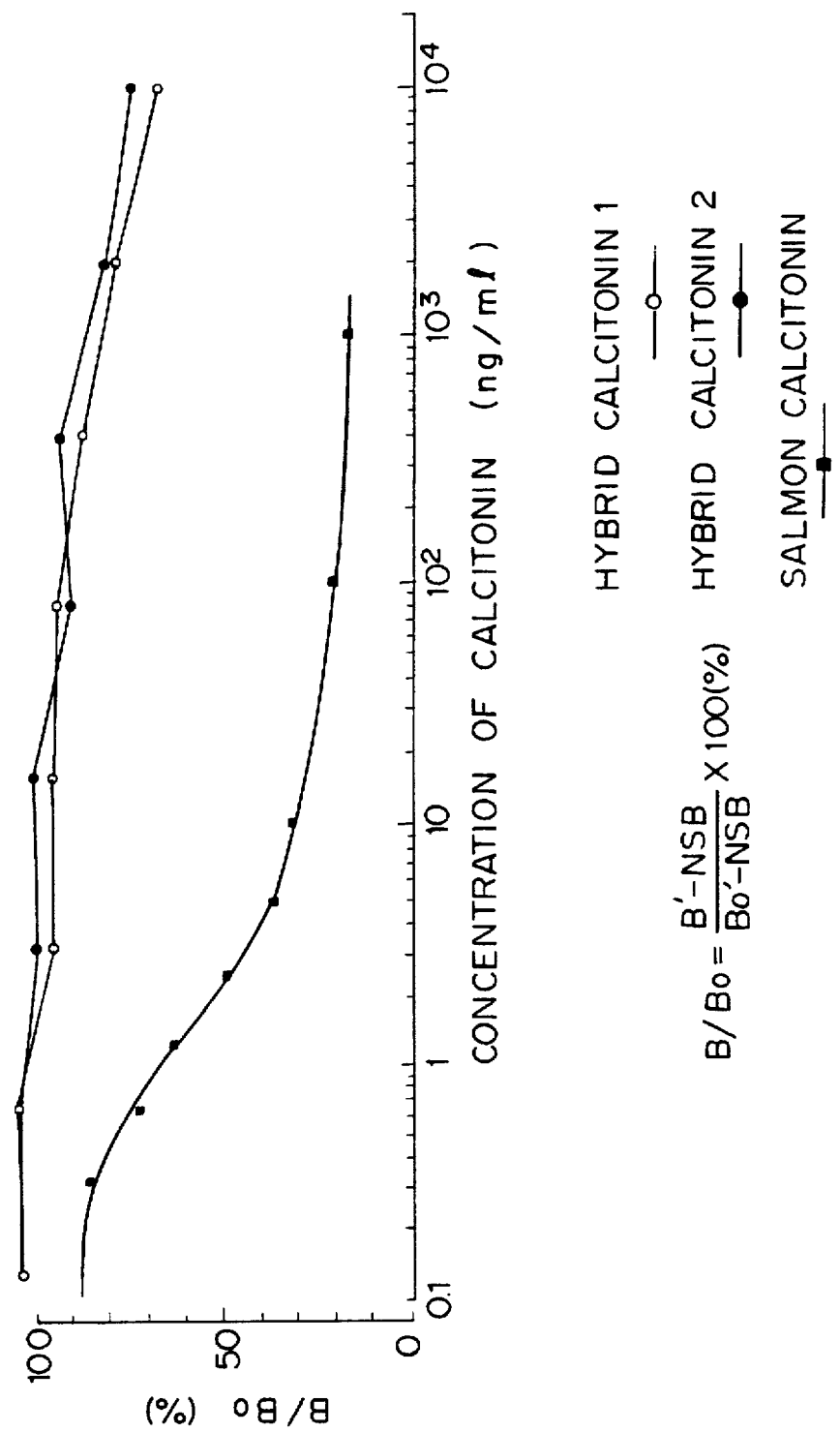

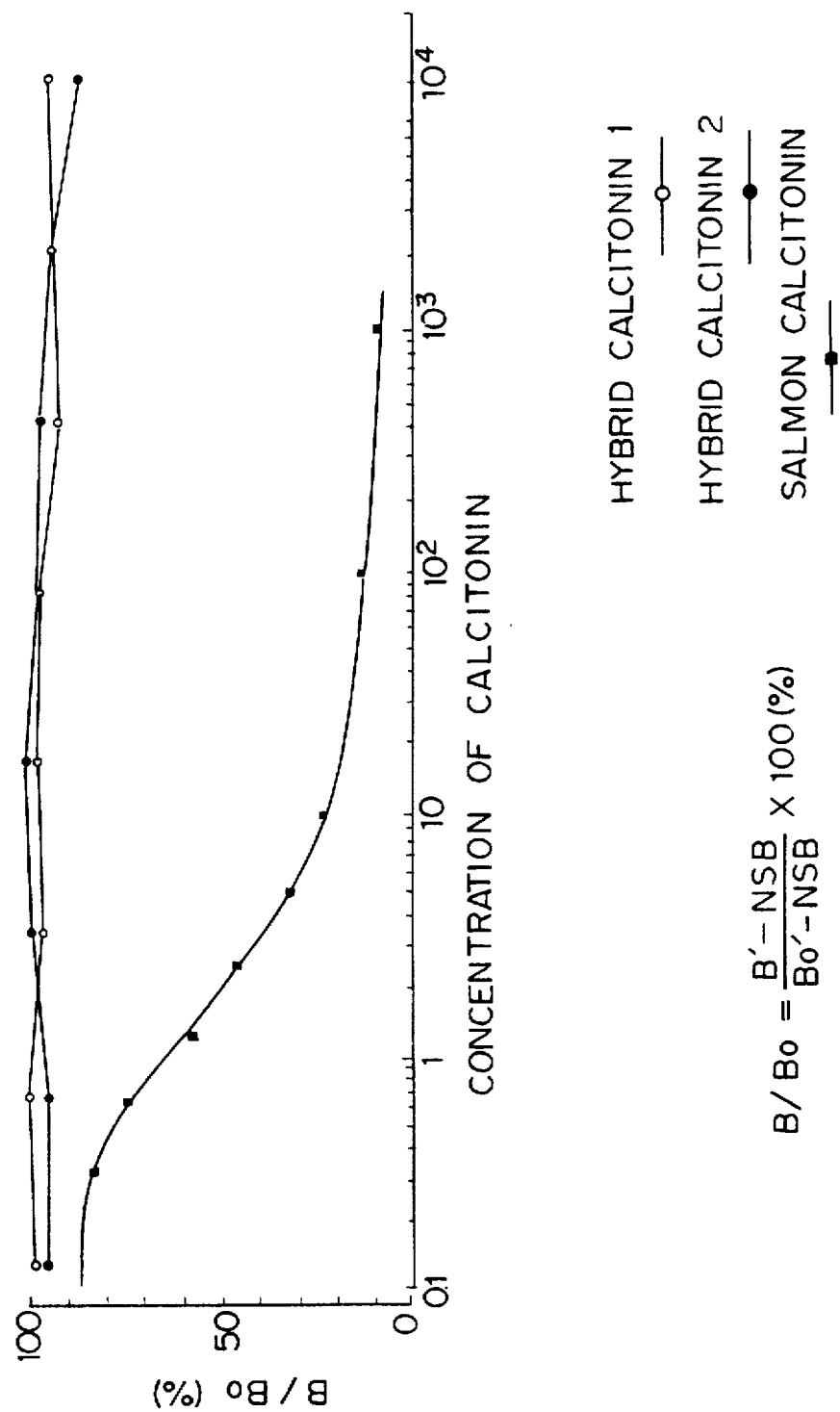

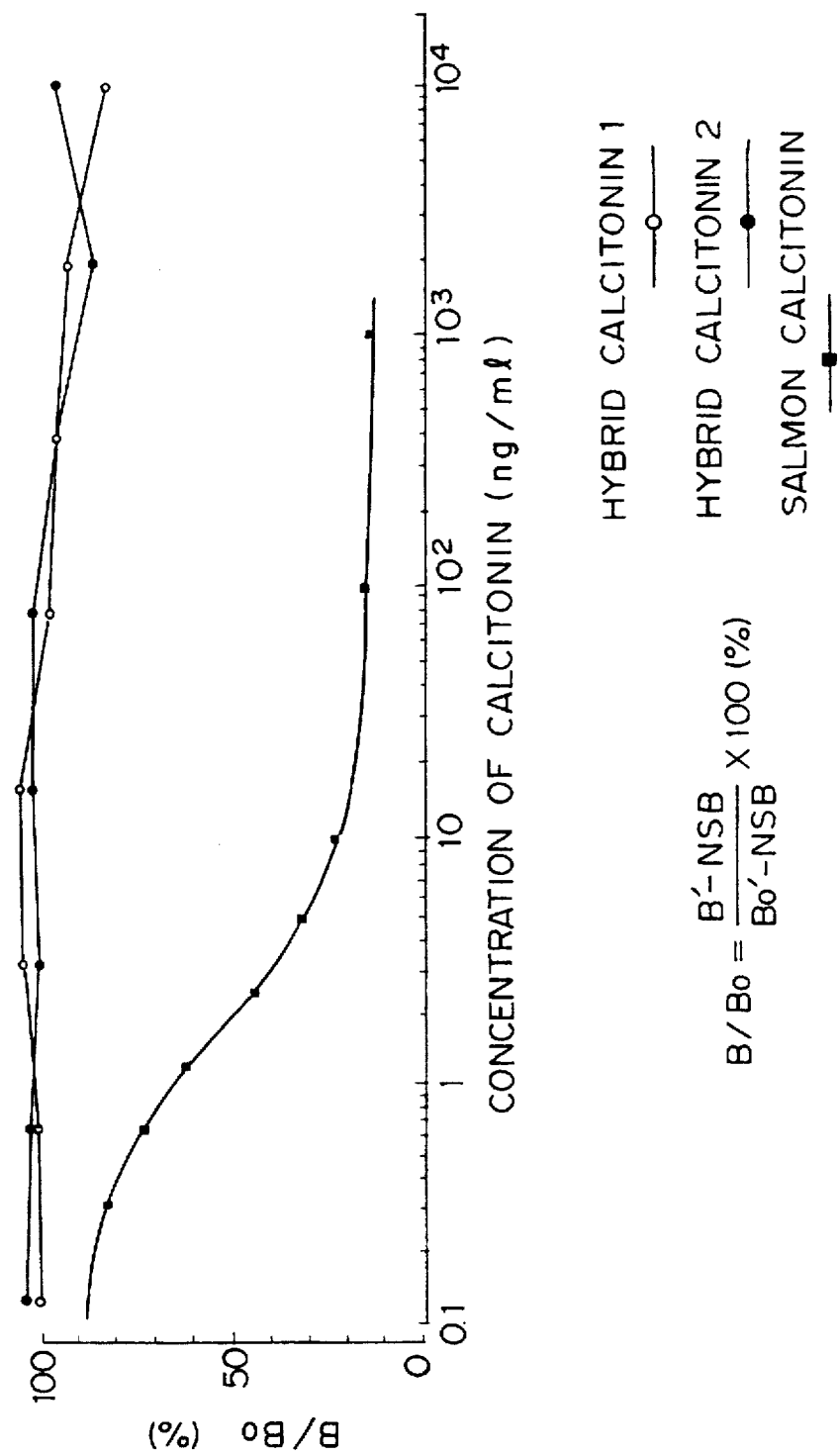

HYBRID CALCITONIN

This application is a continuation od application Ser. No. 07/941,072, filed Oct. 9, 1992, abandoned.

BACKGROUND OF THE INVENTION

This invention relates to novel calcitonin analogs having biological activities.

Calcitonin is known to occur naturally in eel, salmon, chicken, porcine, human, bovine, sheep and rat. Whichever the origin, naturally occurring calcitonin is composed of 32 amino acids. For example, human calcitonin has the following peptide structure, SEQ ID NO:1:

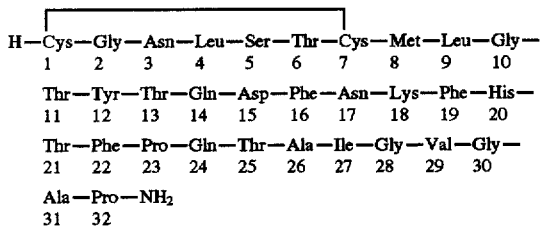

Eel calcitonin has the following peptide structure, SEQ ID NO:2:

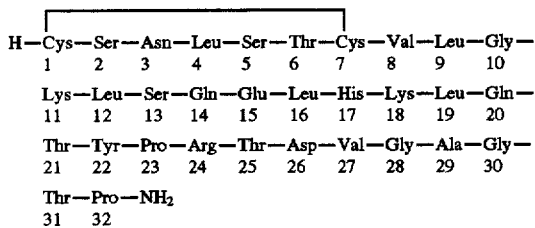

The calcitonin inherently present in humans and animals is hereinafter collectively referred to as "native calcitonin".

Japanese Patent Public Disclosure Nos. 277698/1988, 284198/1988, 287800/1988, J. Biochem. Vol. 159, p. 125 (1986), Endocrinology, Vol. 117, p. 80 (1987) and J. Biochem., Vol. 162, p. 399 (1987) disclose analogs to native calcitonin. Analogs to native calcitonin include: analogs having at least one of the amino acid residues in native calcitonin replaced by another amino acid residue (substitution type); analogs having at least one of the amino acid residues in native calcitonin deleted (deletion type); analogs having at least one amino acid residue added between amino acid residues in native calcitonin or added unto a terminus thereof (addition type); and analogs having two or more of the substitution, deletion and addition types combined together. When two or more amino acid residues are replaced, deleted or added, they may be continuous or spaced apart in the peptide structure. These types of non-native calcitonin are hereinafter referred to as "calcitonin analogs".

Native human calcitonin is inherently present in humans but its biological activities in humans has been shown to be low. On the other hand, native calcitonins derived from animals other than humans such as salmon, eel and chicken have high biological activities for humans and hold promise for use as therapeutics for osteroporosis, neoplastic hypercalcemia and Paget's disease. Furthermore, eel calcitonin analogs have been commercially produced as therapeutics. However, native calcitonin derived from animals other than humans and their analogs cause side effects in humans such as severe nausea, disorders in the functions of the digestive tract, and antigenicity. Human calcitonin has little, if any, of these side effects.

The nausea caused by native calcitonin derived from animals other than humans and analogs thereof is described in the following references:

1) K. Takahashi, et al., "Gan to Kagaku Ryoho (Cancer and Chemotherapy)", Vol. 12, No. 10, 2004–2010 (1985);
2) J. Egawa et al.. "Gan no Rinsho (Clinical Aspects of Cancer)", Vol. 30, No. 3, 251–258 (1984); and
3) G. F. Mazzuoli et al., Calcif. Tissue Int., 38, 3–8 (1986).

The disorders in the functions of the digestive tract caused by native calcitonin derived from animals other than humans and analogs thereof are described in the following references:

1) K. Jonderko, Gut (England), 30, 430–435 (1989);
2) K. Jonderko et al., J. Clin. Gastroenterol., 12, 22–28 (1990); and
3) J. Hotz et al., Digestion, 20, 180–189 (1980).

The antigenicity of native calcitonin derived from animals other than humans and analogs thereof is described in the following references:

1) F. R. Singer et al., J. Clinical Invest., 51, 2331–2338 (1972);
2) J. G. Haddad et al., J. Clinical Invest., 51, 3133–3141 (1972); and
3) A. Grauer et al., J. Bone and Mineral Res., 5, 387–391 (1990).

SUMMARY OF THE INVENTION

The present invention has its object providing novel calcitonin analogs that have not previously been known in the art. Briefly stated, the present invention provides calcitonin that has high biological activities for humans and yet which causes little side effects in humans. The calcitonin of the present invention is a hybrid of human calcitonin and calcitonin derived from animals other than humans, namely, a hybrid calcitonin composed of a peptide segment in human calcitonin and a peptide segment in calcitonin derived from animals other than humans.

The present inventors found that the activity of side effects caused in humans by calcitonin derived from animals other than humans is located predominantly at the amino terminal end, particularly in the peptide segment consisting of 1–16 terminal amino acid residues. It was also found that while all of these 16 terminal amino acid residues may be replaced, the undesired side effects could be eliminated by replacing at least 10 of such amino acid residues.

For the major biological activities of calcitonin derived from humans and from animals other than humans, the amino acid sequence at the carboxyl terminal end is important, as described in the following references:

1) René Maier et al., FEBS Letters, 48, 68 (1974);
2) René Maier et al., Clinical Endocrinology, 5, 3275 (1976);
3) R. M. Epand et al., Eur. J. Brochom., 159, 125 (1986); and
4) D. M. Findlay et al., Endocrinology, 117, 399 (1987).

The present inventors found that the peptide segment specified above, namely, the peptide segment at the carboxyl terminal end having major biological activities, had no active sites that would cause undesired side effects in humans and developed a hybrid calcitonin based on this finding. Hence, from the viewpoint of a reduction in side effects, the peptide segment consisting of amino acid residues in the 11th and subsequent positions towards the carboxyl terminal end may comprise either human calcitonin or calcitonin derived from animals other than humans.

On the other hand, from the viewpoint of biological activities, calcitonin having higher biological activities than human calcitonin is preferred. Hence, the peptide segment closer to the carboxyl terminal end is preferably a peptide segment that is derived from animals other than humans and that has higher biological activities for humans than human calcitonin. In this respect, the peptide segment under consideration has at least 4 amino acid residues, and preferably at least 10 amino acid residues.

From the viewpoints described above, the hybrid calcitonin of the present invention consists of two peptide segments, one comprising the 1st to the 10th amino acid residues from the amino terminal end that is a segment in calcitonin derived from humans and the others comprising the 29th to the 32nd amino acid residues towards the carboxyl terminal end, that is, a segment in calcitonin derived from animals other than humans, with the intermediate peptide segment composed of the 11th to the 28th amino acid residues having the amino acid sequence of either type of calcitonin. If desired, there may be a transition from the amino acid sequence of human calcitonin to that of non-human calcitonin at any position of the peptide segment between the 11th and 28th amino acid residues.

In order to achieve a further reduction in side effects, the peptide segment at the amino terminal end is preferably composed of the 1st to the 13th amino acid residues of human calcitonin. In order to achieve a further enhancement of biological activities, the peptide segment in the 22nd to the 32nd positions is preferably composed of a peptide segment derived from animals other than humans. The peptide segment from the 14th to the 21st positions at the amino terminal end may have the amino acid sequence of either type of calcitonin, and there may be a transition from the amino acid sequence of human calcitonin to that of non-human calcitonin at any position of that intermediate segment. In the most preferred case, the hybrid calcitonin of the present invention is composed of a peptide segment from human calcitonin in the 1st to 16th positions at the amino terminal end, and a peptide segment in non-human calcitonin from the 17th to the 32nd positions.

BRIEF DESCRIPTION OF THE DRAWINGS

FIGS. 6–9 are graphs showing the efficiency of the binding of salmon calcitonin and two hybrid calcitonins to anti-salmon calcitonin human sera.

DETAILED DESCRIPTION OF THE INVENTION

Figure 1:
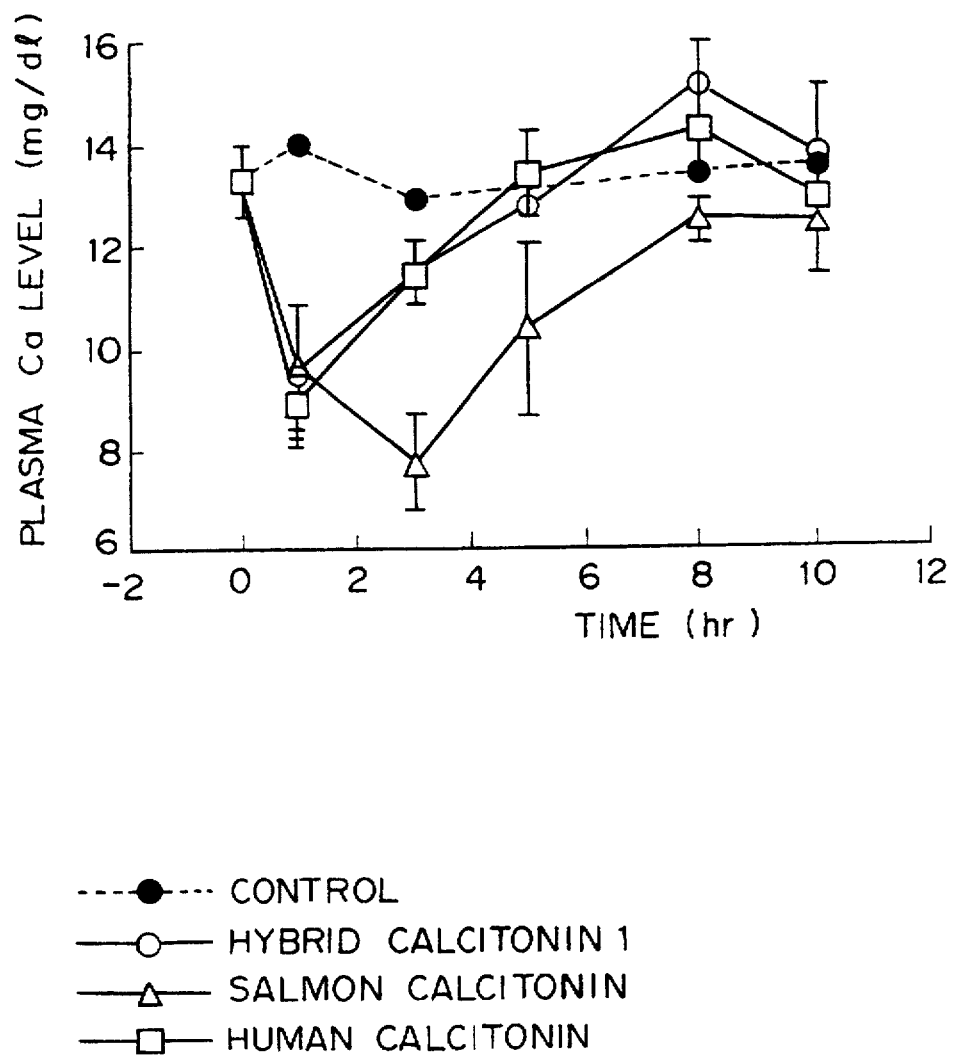
FIG. 1 is a graph showing the time-dependent profile of calcium concentration in blood plasma during treatment with various types of calcitonin.

The term "human calcitonin" as used herein means both native human calcitonin and non-native human calcitonin analogs. In a similar way, the term "non-human calcitonin or calcitonin derived from animals other than humans" means both native calcitonin derived from animals other than humans and non-native analogs of that non-human calcitonin. Animals other than humans preferably include, but are not limited to, salmon, eel and chicken. The number of substituted, deleted or added amino acid residues in the two types of calcitonin analogs is not limited to any particular value but preferably it is no more than 5. If a peptide segment of interest contains no more than 5 amino acid residues, the number of substituted, deleted or added amino acid residues is preferably no more than one, and if that peptide segment contains no more than 10 amino acid residues, the corresponding number of substituted, deleted or added amino acid residues is preferably no more than 3.

In the case of the peptide segment of human calcitonin, the sequence of the first 10 amino acid residues from the amino terminal end is preferably the same as that of native human calcitonin, or it may be that the peptide segment of a human calcitonin analog has the same amino acid sequence as native human calcitonin except that the methionine residue in position 8 is replaced by a valine residue. As for the overall peptide segment of human calcitonin, a preferred analog is such that no more than two amino acid residues are substituted for, deleted from, or added to native calcitonin. The most preferred analog is such that the peptide segment taken as a whole differs from the native type only in the substitution at the methionine residue in position 8.

In the case of the peptide segment of calcitonin derived from animals other than humans, it is preferably the same as the peptide segment of corresponding native calcitonin, or it may be the peptide segment of a non-human calcitonin analog that has no more than 3 amino acid residues substituted for, deleted from or added to the native type. A more preferred analog is such that the peptide segment, taken as a whole, has a sequence in which only one amino acid residue is substituted or deleted from the native type.

Preferred animals other than humans are such that the derived calcitonin has higher biological activities for humans. Examples of such animals include fishes, such as salmon and eel, and birds, such as chicken. Salmon and eel are more preferred, with salmon being particularly preferred.

In consideration of these facts, the hybrid calcitonin of the present invention preferably has the following amino acid sequence, SEQ ID NO:3:

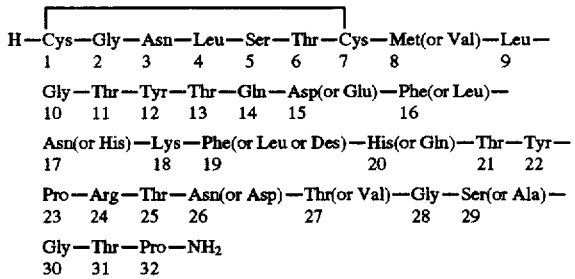

In the hybrid calcitonin of the present invention, the part of the structure of whole calcitonin derived from animals other than humans such as salmon, eel and chicken which causes side effects when administered to humans (e.g. nausea, disorders in the functions of the digestive tract and antigenicity) is replaced by the corresponding segment of human calcitonin causing no such side effects, whereby the side effects caused by the former part are reduced or entirely eliminated. This is equivalent to saying that the hybrid calcitonin of the present invention has the pharmacologically active site of human calcitonin replaced by the corresponding segment of non-human calcitonin in order to enhance the desired physiological activities of human calcitonin.

The hybrid calcitonin of the present invention can be synthesized by solid-phase synthesis, using polymer resins, or by liquid-phase synthesis, which is commonly employed in the art of organic synthesis. The use of solid-phase synthesis is preferred in the case of synthesizing a comparatively small amount of peptides. On the other hand, the use of liquid-phase synthesis is preferred in the case of synthesizing a large amount of peptides. In the examples to be described later in this specification, peptides were synthesized by solid-phase synthesis. However, if the hybrid calcitonin of the present invention is to be synthesized in a large quantity, the use of liquid-phase synthesis, which is a well-known technique of peptide synthesis, is preferred.

The usual procedure of liquid-phase synthesis starts with synthesizing at least two partial peptides, each composed of two or more amino acid residues, it then links these partial peptides either successively and finally obtains the desired peptide having the above-specified amino acid sequence (in the case of the present invention, the desired peptide is the hybrid calcitonin already described above). The liquid-phase synthesis is further characterized by performing the reaction of peptide synthesis in a liquid medium, particularly in a medium such as dimethylformamide or tetrahydrofuran. A partial peptide is typically composed of 2–20, preferably 3–15, amino acid residues. In a preferred case, about 2–10 units of these partial peptides are synthesized and then linked successively to synthesize the desired peptide.

In the peptide synthesis described above, reactive derivatives of amino acids are typically used as starting materials. If the starting amino acid contains active functional groups other than those which form peptide bonds, those active functional groups are preferably protected with protective groups, which are removed after the end of peptide synthesis. The peptide to be produced in the present invention has a 1–7 disulfide bond, which is formed at any desired stage following the synthesis of a partial peptide having a 1–7 sequence. However, this disulfide bond has low stability and is preferably formed after the end of peptide synthesis. These conditions for the procedures of protection and deprotection and the formation of a disulfide bond are also preferably adopted in the solid-phase synthesis to be described below.

Solid-phase synthesis is a method of synthesizing a peptide having the desired amino acid sequence by bonding amino acid residues successively onto a carrier resin. This method can be performed automatically with an automatic synthesizer.

Resins that can be used in solid-phase synthesis include chloromethyl resins, oxymethyl resins, 4-(oxymethyl) phenylacetamidomethyl resins, benzhydrylamine resins and polyacrylamide resins.

The amino acids used in these syntheses are protected amino acids, as required. Exemplary α-amino protecting groups include a carbobenzoxy group (Z), a tertiary butyloxycarbonyl group (Boc), a 9-fluorenylmethyloxycarbonyl group (Fmoc), a formyl group (HOC) and an acetyl group (Ac). Exemplary α-carboxy protecting groups include a benzyl group (Bzl), a tertiary butyl group (Bu$^t$), a methyl group (Me), an ethyl group (Et) and a phenacyl group (Pac). Groups that can be used to protect functional groups in side chains of amino acids include: a benzyl group (Bzl), a p-toluenesulfonyl group (Tos), a p-nitrophenol group (NO$_2$), a benzhydryl group (Bzh), an acetamidomethyl group (Acm), a tertiary butyl group (Bu$^t$), a tertiary butyloxycarbonyl group (Boc), a cyclohexyl group (CHex) and a 4-methoxy-2,3,6-trimethylbenzenesulfonyl group (Mtr).

One or more of these protecting groups may be used depending on the object to be attained.

The sequential addition reaction of amino acids can be performed by dehydrative condensation using carbodiimides or with the aid of active esters. Useful carbodiimides include dicyclohexylcarbodiimide and 1-ethyl 3-(3dimethylaminopropyl)carbodiimide, and useful active esters include an N-hydroxysuccinimide ester (—OSu), a pentafluorophenol ester (—OPfp) and a dihydroxobenztriazine ester (—ODhbt).

Reaction catalysts that can be used include: DMF, THF, dichloromethane, chloroform, ethyl acetate, dioxane, DMSO, N-methylpyrrolidone, pyridine and water.

Various deprotecting agents may be used depending on the type of protective groups to be eliminated and the object to be achieved, and useful examples include: hydrogen fluoride, trifluoroacetic acid, trifluoromethanesulfonic acid, ammonia/methanol, hydrogen bromide/acetic acid, hydrogen/palladium on carbon, mercury acetate, acetic acid/zinc powder, and alkali/water-methanol.

During or after synthesis, various techniques of purification can be employed, such as reverse-phase chromatography, normal-phase chromatography, ion-exchange chromatography and gel filtration chromatography, and recrystallization. Disulfide bonds may be formed by oxidation with atmospheric air or potassium ferricyanide.

The following examples are provided for the purpose of further illustrating the present invention, but are in no way to be taken as limiting.

Examples 1–6 illustrate the synthesis of samples of the hybrid calcitonin of the present invention, and Example 7 shows the results of analysis of amino acid composition for the calcitonin samples synthesized in Examples 1–6. Examples 8–10 describe the experiments conducted to evaluate the principal activities of the hybrid calcitonin of the present invention. Examples 11–14 describe the experiments conducted to demonstrate elimination of the side effects of calcitonin.

EXAMPLE 1

Synthesis of (1–16) human/(17–32) salmon hybrid calcitonin, SEQ ID NO:4:

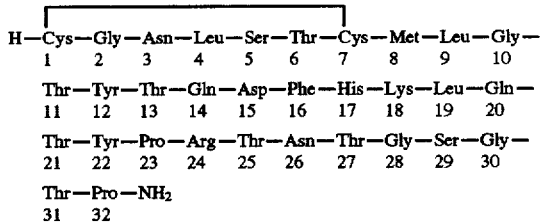

Synthesis was performed by a solid-phase synthesis method using an automatic synthesizer.

(I) Introducing proline onto benzhydrylamine (BHA) resin

Ten grams of BHA resin (—NH$_2$: 0.38 mmol/g) were suspended and swollen in 100 ml of DMF. After removing the supernatant, an additional 100 ml of DMF was added, followed by addition of BocProOH (15 mmol), DCC (20 mmol) and HOBT (20 mmol). The mixture was shaken overnight at room temperature. After filtration with a glass filter, the resulting resin was washed with methylene chloride.

Subsequently, 200 ml of a methylene chloride solution containing 10 v/v % acetic anhydride was added, and the mixture was shaken at room temperature for 1 h to block the residual amino groups. After completion of the reaction, the resin was washed with methylene chloride and dried under vacuum.

After drying, 50 ml of a methylene chloride solution containing 50 v/v % trifluoroacetic acid was added and the mixture was shaken at room temperature for 1 h. After filtration with a glass filter, the resulting resin was washed successively with methylene chloride, methanol, methylene chloride and triethylamine and dried under vacuum.

(2) Sequential addition reaction of amino acids

One gram of the resin obtained in (1) was packed in the column of an automatic synthesizer, and amino acids were added sequentially under the following conditions.

(i) reaction: 30 min at R.T. in solvent DMF
(ii) washing: 10 min at R.T. with DMF
(iii) Fmoc removal: 10 min at R.T. with 20 v/v % piperidine in solvent DMF
(iv) washing: 10 min at R.T. with DMF By repeating the steps (1)–(4), 31 amino acids following Pro were added. The amino acids used are listed in Table 1 below.

TABLE 1

| | |
|---|---|
| Fmoc-L-Thr(But)-ODhbt | 0.430 g |
| Fmoc-Gly-OPfp | 0.367 |
| Fmoc-L-Ser(But)-ODhbt | 0.419 |
| Fmoc-Gly-OPfp | 0.367 |
| Fmoc-L-Thr(But)-ODhbt | 0.430 |
| Fmoc-L-Asn-OPfp | 0.412 |
| Fmoc-L-Thr(But)-ODhbt | 0.430 |
| Fmoc-L-Arg(Mtr)-OPfp | 0.641 |
| Fmoc-L-Pro-OPfp | 0.400 |
| Fmoc-L-Tyr(But)-OPfp | 0.495 |
| Fmoc-L-Thr(But)-ODhbt | 0.430 |
| Fmoc-L-Gln-OPfp | 0.423 |
| Fmoc-L-Leu-OPfp | 0.411 |
| Fmoc-L-Lys(Boc)-OPfp | 0.503 |
| Fmoc-L-His(Boc)-OPfp | 0.510 |
| Fmoc-L-Phe-OPfp | 0.438 |
| Fmoc-L-Asp(OBut)-OPfp | 0.457 |
| Fmoc-L-Gln-OPfp | 0.423 |
| Fmoc-L-Thr(But)-ODhbt | 0.430 |
| Fmoc-L-Tyr(But)-OPfp | 0.495 |
| Fmoc-L-Thr(But)-ODhbt | 0.430 |
| Fmoc-Gly-OPfp | 0.367 |
| Fmoc-L-Leu-OPfp | 0.411 |
| Fmoc-L-Met-OPfp | 0.426 |
| Fmoc-L-Cys(Trt)-OPfp | 0.595 |
| Fmoc-L-Thr(But)-ODhbt | 0.430 |
| Fmoc-L-Ser(But)-ODhbt | 0.419 |
| Fmoc-L-Leu-OPfp | 0.411 |
| Fmoc-L-Asn-OPfp | 0.412 |
| Fmoc-Gly-OPfp | 0.367 |
| Fmoc-L-Cys(Trt)-OPfp | 0.595 |

After the reaction, the protective groups and the resin were removed from the peptide with hydrogen fluoride, and the peptide was washed with ether. The precipitate was dissolved in an aqueous solution of 50 v/v % acetic acid, and the insoluble matter was filtered off. The filtrate was freeze-dried to obtain ca. 600 mg of crude peptide.

(3) Purification and the formation of disulfide bonds

A portion (ca. 500 mg) of the crude peptide was dissolved in water containing 0.1 v/v % TFA and the solution was subjected to high-performance liquid chromatography on an ODS column.

Using solution A (acetonitrile containing 0.1 v/v % TFA) and solution B (water containing 0.1 v/v % TFA), the column was eluted with the stepwise gradient (A/B in v/v %) increasing from 20 through 30 to 40%, and fractions at 30% elution were collected and freeze-dried.

The freeze-dried peptide (46 mg) was dissolved in 50 ml of 0.05 v/v % acetic acid and the pH of the solution was adjusted to 8.5 with 3M aqueous ammonia. Subsequently, 1.5ml of 0.1M $K_3Fe(CN)_6$ was added and the mixture was stirred at room temperature for 30 min to form disulfide bonds. After adjusting the pH to 5.0 with 50% acetic acid, an anion exchange resin ($Cl^-$ form) was added and the mixture was stirred for 20 min, followed by filtering off of the resin.

The filtrate was concentrated and subjected to high-performance liquid chromatography on an ODS column and purified again by the same procedure as described above. Fractions at 30% elution were collected and freeze-dried to obtain 28 mg of the desired peptide.

EXAMPLE 2

Synthesis of (1–16) human/(17–32) eel hybrid calcitonin, SEQ ID NO:5:

H—Cys—Gly—Asn—Leu—Ser—Thr—Cys—Met—Leu—Gly—
  1    2    3    4    5    6    7    8    9   10
Thr—Tyr—Thr—Gln—Asp—Phe—His—Lys—Leu—Gln—
 11   12   13   14   15   16   17   18   19   20
Thr—Tyr—Pro—Arg—Thr—Asp—Val—Gly—Ala—Gly—
 21   22   23   24   25   26   27   28   29   30
Thr—Pro—$NH_2$
 31   32

(1) Sequential addition reaction of amino acids

One gram of the proline-incorporating BHA resin prepared in step (1) of Example 1 was packed in the column of an automatic synthesizer and amino acids were added under the same reaction conditions as used in step (2) of Example 1. The amino acids used are listed in Table 2 below.

TABLE 2

| | |
|---|---|
| Fmoc-L-Thr(But)-ODhbt | 0.430 g |
| Fmoc-Gly-OPfp | 0.367 |
| Fmoc-L-Ala-OPfp | 0.378 |
| Fmoc-Gly-OPfp | 0.367 |
| Fmoc-L-Val-OPfp | 0.400 |
| Fmoc-L-Asp(OBut)-OPfp | 0.457 |
| Fmoc-L-Thr(But)-ODhbt | 0.430 |
| Fmoc-L-Arg(Mtr)-OPfp | 0.641 |
| Fmoc-L-Pro-OPfp | 0.400 |
| Fmoc-L-Tyr(But)-OPfp | 0.495 |
| Fmoc-L-Thr(But)-ODhbt | 0.430 |
| Fmoc-L-Gln-OPfp | 0.423 |
| Fmoc-L-Leu-OPfp | 0.411 |
| Fmoc-L-Lys(Boc)-OPfp | 0.503 |
| Fmoc-L-His(Boc)-OPfp | 0.510 |
| Fmoc-L-Phe-OPfp | 0.438 |
| Fmoc-L-Asp(OBut)-OPfp | 0.457 |
| Fmoc-L-Gln-OPfp | 0.423 |
| Fmoc-L-Thr(But)-ODhbt | 0.430 |
| Fmoc-L-Tyr(But)-OPfp | 0.495 |
| Fmoc-L-Thr(But)-ODhbt | 0.430 |
| Fmoc-Gly-OPfp | 0.367 |
| Fmoc-L-Leu-OPfp | 0.411 |
| Fmoc-L-Met-OPfp | 0.426 |
| Fmoc-L-Cys(Trt)-OPfp | 0.595 |
| Fmoc-L-Thr(But)-ODhbt | 0.430 |
| Fmoc-L-Ser(But)-ODhbt | 0.419 |
| Fmoc-L-Leu-OPfp | 0.411 |
| Fmoc-L-Asn-OPfp | 0.412 |
| Fmoc-Gly-OPfp | 0.367 |
| Fmoc-L-Cys(Trt)-OPfp | 0.595 |

After the reaction, the peptide-resin was treated by the same method as described in step (2) of Example 1 to give ca. 510 mg of crude peptide.

(2) Purification and the formation of disulfide bonds

A portion (ca. 450 mg) of the crude peptide was subjected to purification and the formation of disulfide bonds by the same procedures as used in step (3) of Example 1, whereby 32 mg of purified peptide were obtained.

EXAMPLE 3

Synthesis of (1–16, Met$^8$→Val$^8$) human analog/(17–32) eel hybrid calcitonin, SEQ ID NO:6:

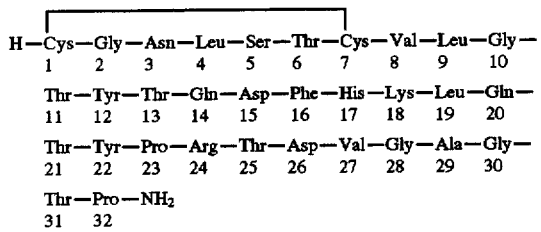

(1) Sequential addition reaction of amino acids

One gram of the proline-incorporating BHA resin prepared in step (1) of Example 1 was packed in the column of an automatic synthesizer and amino acids were added under the same reaction conditions as used in step (2) of Example 1. The amino acids used are listed in Table 3 below.

TABLE 3

| | |
|---|---|
| Fmoc-L-Thr(But)-ODhbt | 0.430 g |
| Fmoc-Gly-OPfp | 0.367 |
| Fmoc-L-Ala-OPfp | 0.378 |
| Fmoc-Gly-OPfp | 0.367 |
| Fmoc-L-Val-OPfp | 0.400 |
| Fmoc-L-Asp(OBut)-OPfp | 0.457 |
| Fmoc-L-Thr(But)-ODhbt | 0.430 |
| Fmoc-L-Arg(Mtr)-OPfp | 0.641 |
| Fmoc-L-Pro-OPfp | 0.400 |
| Fmoc-L-Tyr(But)-OPfp | 0.495 |
| Fmoc-L-Thr(But)-ODhbt | 0.430 |
| Fmoc-L-Gln-OPfp | 0.423 |
| Fmoc-L-Leu-OPfp | 0.411 |
| Fmoc-L-Lys(Boc)-OPfp | 0.503 |
| Fmoc-L-His(Boc)-OPfp | 0.510 |
| Fmoc-L-Phe-OPfp | 0.438 |
| Fmoc-L-Asp(OBut)-OPfp | 0.457 |
| Fmoc-L-Gln-OPfp | 0.423 |
| Fmoc-L-Thr(But)-ODhbt | 0.430 |
| Fmoc-L-Tyr(But)-OPfp | 0.495 |
| Fmoc-L-Thr(But)-ODhbt | 0.430 |
| Fmoc-Gly-OPfp | 0.367 |
| Fmoc-L-Leu-OPfp | 0.411 |
| Fmoc-L-Val-OPfp | 0.400 |
| Fmoc-L-Cys(Trt)-OPfp | 0.595 |
| Fmoc-L-Thr(But)-ODhbt | 0.430 |
| Fmoc-L-Ser(But)-ODhbt | 0.419 |
| Fmoc-L-Leu-OPfp | 0.411 |
| Fmoc-L-Asn-OPfp | 0.412 |
| Fmoc-Gly-OPfp | 0.367 |
| Fmoc-L-Cys(Trt)-OPfp | 0.595 |

After the reaction, the peptide-resin was treated by the same method as described in step (2) of Example 1 to give ca. 580 mg of crude peptide.

(2) Purification and the formation of disulfide bonds

A portion (ca. 500 mg) of the crude peptide was subjected to purification and the formation of disulfide bonds by the same procedures as used in (3) of Example 1, whereby 35 mg of purified peptide were obtained.

EXAMPLE 4

Synthesis of (1–16) human/(17–31, Des Leu$^{19}$) eel analog hybrid calcitonin, SEQ ID NO:7:

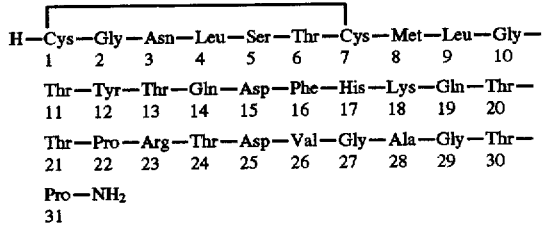

(1) Sequential addition reaction of amino acids

One gram of the proline-incorporating BHA resin prepared in step (1) of Example 1 was packed in the column of an automatic synthesizer and amino acids were added under the same reaction conditions as used in step (2) of Example 1. The amino acids used are listed in Table 4 below.

TABLE 4

| | |
|---|---|
| Fmoc-L-Thr(But)-ODhbt | 0.430 g |
| Fmoc-Gly-OPfp | 0.367 |
| Fmoc-L-Ala-OPfp | 0.378 |
| Fmoc-Gly-OPfp | 0.367 |
| Fmoc-L-Val-OPfp | 0.400 |
| Fmoc-L-Asp(OBut)-OPfp | 0.457 |
| Fmoc-L-Thr(But)-ODhbt | 0.430 |
| Fmoc-L-Arg(Mtr)-OPfp | 0.641 |
| Fmoc-L-Pro-OPfp | 0.400 |
| Fmoc-L-Tyr(But)-OPfp | 0.495 |
| Fmoc-L-Thr(But)-ODhbt | 0.430 |
| Fmoc-L-Gln-OPfp | 0.423 |
| Fmoc-L-Lys(Boc)-OPfp | 0.503 |
| Fmoc-L-His(Boc)-OPfp | 0.510 |
| Fmoc-L-Phe-OPfp | 0.438 |
| Fmoc-L-Asp(OBut)-OPfp | 0.457 |
| Fmoc-L-Gln-OPfp | 0.423 |
| Fmoc-L-Thr(But)-ODhbt | 0.430 |
| Fmoc-L-Tyr(But)-OPfp | 0.495 |
| Fmoc-L-Thr(But)-ODhbt | 0.430 |
| Fmoc-Gly-OPfp | 0.367 |
| Fmoc-L-Leu-OPfp | 0.411 |
| Fmoc-L-Met-OPfp | 0.426 |
| Fmoc-L-Cys(Trt)-OPfp | 0.595 |
| Fmoc-L-Thr(But)-ODhbt | 0.430 |
| Fmoc-L-Ser(But)-ODhbt | 0.419 |
| Fmoc-L-Leu-OPfp | 0.411 |
| Fmoc-L-Asn-OPfp | 0.412 |
| Fmoc-Gly-OPfp | 0.367 |
| Fmoc-L-Cys(Trt)-OPfp | 0.595 |

After the reaction, the peptide-resin was treated by the same method as described in step (2) of Example 1 to obtain ca. 520 mg of crude peptide.

(2) Purification and the formation of disulfide bonds

A portion (ca. 450 mg) of the crude peptide was subjected to purification and the formation of disulfide bonds by the same procedures as used in step (3) of Example 1, whereby 23 mg of purified peptide were obtained.

EXAMPLE 5

Synthesis of (1–13) human/(14–32) salmon hybrid calcitonin, SEQ ID NO:8:

```
   ┌─────────────────────────────────────────┐
H—Cys—Gly—Asn—Leu—Ser—Thr—Cys—Met—Leu—Gly—
   1    2    3    4    5    6    7    8    9   10
   Thr—Tyr—Thr—Gln—Glu—Leu—His—Lys—Leu—Gln—
   11   12   13   14   15   16   17   18   19   20
   Thr—Tyr—Pro—Arg—Thr—Asn—Thr—Gly—Ser—Gly—
   21   22   23   24   25   26   27   28   29   30
   Thr—Pro—NH₂
   31   32
```

Synthesis was performed by a solid-phase synthesis method using an automatic synthesizer.

(1) Introducing proline into benzhydrylamine (BHA) resin

Ten grams of BHA resin (—NH$_2$: 0.38 mmol/g) was suspended and swollen in 100 ml of DMF. After removing the supernatant, an additional 100 ml of DMF were added, followed by addition of BocProOH (19 mmol), DCC (19 mmol) and HOBT (19 mmol). The mixture was shaken overnight at room temperature. After filtration with a glass filter, the resulting resin was washed with methylene chloride. Subsequently, 200 ml of a methylene chloride solution containing 10 v/v % acetic anhydride was added and the mixture was stirred at room temperature for 1 h to block the residual amino groups. After completion of the reaction, the mixture was washed with methylene chloride and dried under vacuum.

After drying, 50 ml of a methylene chloride solution containing 50 v/v % trifluoroacetic acid was added and the mixture was stirred at room temperature for 1 h. After filtration with a glass filter, the resulting resin was washed successively with methylene chloride, methanol, methylene chloride and triethylamine, and dried under vacuum.

A portion of the resulting resin was analyzed with an amino acid analyzer and it was found that 0.31 mmol of proline had been incorporated per gram of the resin.

(2) Sequential addition reaction of amino acids

One gram of the resin obtained in step (1) was packed in the column of an automatic synthesizer and amino acids were added sequentially under the following conditions.

(i) addition reaction: 30 min at R.T. in solvent DMF
(ii) washing: 10 min at R.T. with DMF
(iii) Fmoc removal: 10 min at R.T. with 20 v/v % piperidine in solvent DMF
(iv) washing: 10 min at R.T. with DMF By repeating the steps (1)–(4), 31 amino acids following Pro were added. The amino acids used are listed in Table 5 below.

TABLE 5

| | |
|---|---|
| Fmoc-L-Thr(But)-ODhbt | 0.430 g |
| Fmoc-Gly-OPfp | 0.367 |
| Fmoc-L-Ser(But)-ODhbt | 0.419 |
| Fmoc-Gly-OPfp | 0.367 |
| Fmoc-L-Thr(But)-ODhbt | 0.430 |
| Fmoc-L-Asn-OPfp | 0.412 |
| Fmoc-L-Thr(But)-ODhbt | 0.430 |
| Fmoc-L-Arg(Mtr)-OPfp | 0.641 |
| Fmoc-L-Pro-OPfp | 0.400 |
| Fmoc-L-Tyr(But)-OPfp | 0.495 |
| Fmoc-L-Thr(But)-ODhbt | 0.430 |
| Fmoc-L-Gln-OPfp | 0.423 |
| Fmoc-L-Leu-OPfp | 0.411 |
| Fmoc-L-Lys(Boc)-OPfp | 0.503 |
| Fmoc-L-His(Boc)-OPfp | 0.510 |
| Fmoc-L-Leu-OPfp | 0.411 |
| Fmoc-L-Glu(OBut)-OPfp | 0.468 |
| Fmoc-L-Gln-OPfp | 0.423 |
| Fmoc-L-Thr(But)-ODhbt | 0.430 |

TABLE 5-continued

| | |
|---|---|
| Fmoc-L-Tyr(But)-OPfp | 0.495 |
| Fmoc-L-Thr(But)-ODhbt | 0.430 |
| Fmoc-Gly-OPfp | 0.367 |
| Fmoc-L-Leu-OPfp | 0.411 |
| Fmoc-L-Met-OPfp | 0.426 |
| Fmoc-L-Cys(Trt)-OH | 0.464 |
| Fmoc-L-Thr(But)-ODhbt | 0.430 |
| Fmoc-L-Ser(But)-ODhbt | 0.419 |
| Fmoc-L-Leu-OPfp | 0.411 |
| Fmoc-L-Asn-OPfp | 0.412 |
| Fmoc-Gly-OPfp | 0.367 |
| Fmoc-L-Cys(Trt)-OH | 0.464 |

After the reaction, the resin and the protective groups were removed from the peptide with hydrogen fluoride and the peptide was washed with ether. The precipitate was dissolved in an aqueous solution of 50 v/v % acetic acid and the insoluble matter was filtered off. The filtrate was freeze-dried to obtain ca. 720 mg of crude peptide.

(3) Purification and the formation of disulfide bonds

A portion (ca. 700 mg) of the crude peptide was dissolved in water containing 0.1 v/v % TFA and the solution was subjected to high-performance liquid chromatography on an ODS column.

Using a solvent system consisting of water and acetonitrile containing 0.1% TFA, the column was eluted with a stepwise gradient of acetonitrile increasing from 20 v/v % through 30 v/v % to 40 v/v %, and fractions at 30 v/v % elution were collected and freeze-dried (primary purification).

The freeze-dried peptide (ca. 80 mg) was dissolved in 80 ml of 0.05 v/v % acetic acid and the pH of the solution was adjusted to 8.5 with 3M aqueous ammonia. Subsequently, 1.5 ml of 0.1M K$_3$Fe(CN)$_6$ was added and the mixture was stirred at room temperature for 30 min to form disulfide bonds. After adjusting the pH to 5.0 with 50 v/v % acetic acid, an anion exchange resin (Cl$^-$ form) was added and the mixture was stirred for 20 min, followed by filtering off the resin.

The filtrate was concentrated and subjected again to high-performance liquid chromatography on an ODS column, which was eluted with the same solvent system as used in the primary purification at stepwise density gradients of acetonitrile from 25, 27 through 30 to 35 v/v % (secondary purification). Fractions at 30 v/v % elution were collected and freeze-dried to obtain 53 mg of the titled peptide.

EXAMPLE 6

Synthesis of (1–21) human/(22–32) salmon hybrid calcitonin, SEQ ID NO:9:

```
   ┌─────────────────────────────────────────┐
H—Cys—Gly—Asn—Leu—Ser—Thr—Cys—Met—Leu—Gly—
   1    2    3    4    5    6    7    8    9   10
   Thr—Tyr—Thr—Gln—Asp—Phe—Asn—Lys—Phe—His—
   11   12   13   14   15   16   17   18   19   20
   Thr—Tyr—Pro—Arg—Thr—Asn—Thr—Gly—Ser—Gly—
   21   22   23   24   25   26   27   28   29   30
   Thr—Pro—NH₂
   31   32
```

One gram of the proline-incorporating BHA resin prepared in step (1) of Example 5 was packed in the column of an automatic synthesizer and amino acids were added under the same reaction conditions as used in step (2) of Example 5. The amino acids used are listed in Table 6 below.

TABLE 6

| Fmoc-L-Thr(But)-ODhbt | 0.430 g |
|---|---|
| Fmoc-Gly-OPfp | 0.367 |
| Fmoc-L-Ser(But)-ODhbt | 0.419 |
| Fmoc-Gly-OPfp | 0.367 |
| Fmoc-L-Thr(But)-ODhbt | 0.430 |
| Fmoc-L-Asn-OPfp | 0.412 |
| Fmoc-L-Thr(But)-ODhbt | 0.430 |
| Fmoc-L-Arg(Mtr)-OPfp | 0.641 |

TABLE 6-continued

| Fmoc-L-Pro-OPfp | 0.400 |
|---|---|
| Fmoc-L-Tyr(But)-OPfp | 0.495 |
| Fmoc-L-Thr(But)-ODhbt | 0.430 |
| Fmoc-L-His(Boc)-OPfp | 0.510 |
| Fmoc-L-Phe-OPfp | 0.438 |
| Fmoc-L-Lys(Boc)-OPfp | 0.503 |
| Fmoc-L-Asn-OPfp | 0.412 |
| Fmoc-L-Phe-OPfp | 0.438 |
| Fmoc-L-Asp(OBut)-OPfp | 0.457 |
| Fmoc-t-Gln-OPfp | 0.423 |
| Fmoc-L-Thr(But)-ODhbt | 0.430 |
| Fmoc-L-Tyr(But)-OPfp | 0.495 |
| Fmoc-L-Thr(But)-ODhbt | 0.430 |
| Fmoc-Gly-OPfp | 0.367 |
| Fmoc-L-Leu-OPfp | 0.411 |
| Fmoc-L-Met-OPfp | 0.426 |
| Fmoc-L-Cys(Trt)-OPfp | 0.595 |
| Fmoc-L-Thr(But)-ODhbt | 0.430 |
| Fmoc-L-Ser(But)-ODhbt | 0.419 |
| Fmoc-L-Leu-OPfp | 0.411 |
| Fmoc-L-Asp-OPfp | 0.412 |
| Fmoc-Gly-OPfp | 0.367 |
| Fmoc-L-Cys(Trt)-OPfp | 0.595 |

After the reaction, the peptide-resin was treated by the same method as used in step (2) of Example 5 to obtain ca. 860 mg of crude peptide.

(2) Purification and the formation of disulfide bonds

A portion (ca. 850 mg) of the crude peptide was subjected to purification and the formation of disulfide bonds by the same procedures as used in step (3) of Example 5.

The resulting filtrate was concentrated and subjected again to high-performance liquid chromatography on an ODS column, which was eluted with the same solvent system as used in the primary purification at stepwise density gradients of acetonitrile from 24 to 35 v/v % through 26, 28 and 30 v/v % (secondary purification). Fractions at 28 v/v % elution were collected and freeze-dried to obtain 66 mg of the desired peptide.

EXAMPLE 7

Analysis of amino acid composition

Each of purified hybrid calcitonin prepared in Examples 1–6 was hydrolyzed at 150° C. for 1 h in the presence of 6N HCl, and the amino acid composition was analyzed with an amino acid analyzer. The results are shown in Table 7.

TABLE 7

| Amino acid | Example 1 | Example 2 | Example 3 | Example 4 | Example 5 | Example 6 |
|---|---|---|---|---|---|---|
| Asx | 3.14(3) | 3.12(3) | 3.12(3) | 3.17(3) | 2.11(2) | 4.50(4) |
| Thr | 6.43(7) | 5.32(6) | 5.44(6) | 5.65(6) | 6.37(7) | 6.86(7) |
| Ser | 1.79(2) | 0.85(1) | 0.82(1) | 0.84(1) | 1.71(2) | 1.64(2) |
| Glx | 2.34(2) | 2.26(2) | 2.35(2) | 2.28(2) | 3.49(3) | 1.00(1) |
| Gly | 4.14(4) | 4.20(4) | 4.14(4) | 4.08(4) | 4.01(4) | 4.57(4) |
| Ala | 0 (0) | 1.01(1) | 1.02(1) | 0.96(1) | 0 (0) | 0 (0) |
| Val | 0 (0) | 1.07(1) | 2.01(2) | 1.12(1) | 0 (0) | 0 (0) |
| Met | 0.97(1) | 0.98(1) | 0 (0) | 0.90(1) | 1.01(1) | 0.93(1) |
| Leu | 3.15(3) | 3.11(3) | 3.10(3) | 2.03(2) | 4.28(4) | 2.00(2) |
| Tyr | 2.02(2) | 2.06(2) | 2.02(2) | 2.06(2) | 2.12(2) | 2.01(2) |
| Phe | 1.04(1) | 1.06(1) | 1.04(1) | 1.07(1) | 0 (0) | 2.07(2) |
| His | 1.02(1) | 1.03(1) | 1.12(1) | 1.08(1) | 1.05(1) | 0.80(1) |
| Lys | 1.03(1) | 1.04(1) | 1.02(1) | 1.06(1) | 1.05(1) | 0.92(1) |
| Arg | 1.01(1) | 1.00(1) | 0.98(1) | 0.99(1) | 0.99(1) | 0.85(1) |
| Pro | 1.97(2) | 1.92(2) | 1.95(2) | 1.69(2) | 1.84(2) | 2.06(2) |

Note: The theoretical values are parenthesized.

EXAMPLE 8

Assaying biological activities

The six novel calcitonins prepared in Examples 1–6 were dissolved in a 0.1M sodium acetate buffer solution (pH 4.2) containing 0.1% BSA (bovine serum albumin) and injected into pre-fasted (24 h) SD male rats (4-wk old) through the tail vein. One hour later, the concentration of serum calcium was measured by the OCPC method (Calcium C—Test Wako of Wako Pure Chemical Industries, Ltd.) The calcitonin activity that caused a 10% drop in the concentration of serum calcium was determined to be 10 mU, and the number of units per milligram of calcitonin was designated "specific activity". The results are shown in Table 8.

TABLE 8

| Novel calcitonin | Specific activity (U/mg) |
|---|---|
| Example 1 | 2106* |
| 2 | 2639 |
| 3 | 2262 |
| 4 | 2611 |
| 5 | 2575 |
| 6 | 1792 |

*Average for two measurements

EXAMPLE 9

Efficacy of calcitonins against hypercalcemia
Method

Vitamin $D_3$ (5 mg/kg) was administered orally to 5-wk old SD male rats for 4 consecutive days to construct experimental models of hypercalcemic rats. On day 5, (1–16) human/(17–32) salmon hybrid calcitonin (hybrid calcitonin 1), salmon calcitonin and human calcitonin were injected subcutaneously, each in an amount of 4 IU/kg. Blood was sampled at given time intervals and the concentration of calcium in plasma was measured.

Results and Discussion

The time-dependent profiles of plasma calcium concentrations for the test calcitonins are shown in FIG. 1. As one can see from FIG. 1, all of the hybrid calcitonin 1, salmon calcitonin and human calcitonin tested caused rapid reduction in the elevated blood calcium concentration. It is therefore clear that the hybrid calcitonin of the present invention is as effective as salmon calcitonin and human calcitonin against hypercalcemia.

EXAMPLE 10

Analgesic effect of calcitonins

Method i) Animal

Ten male rabbits (Kbl:JW) weighing 2.7–3.2 kg were used.

ii) Implantation of a guide cannula for intraventricular administration

The rabbits were secured in a stereotaxic apparatus under anesthesia with pentobarbital (30 mg/kg, i.v.). After the scalp was incised, a guide cannula for intraventricular administration (Plastic Products) was inserted into the left lateral ventricle of each animal and fixed with dental cement (stereotaxic coordinates from bregma: posterior, 4.0 mm; lateral, 5.5 mm; ventral, 5.5 mm). After 1-wk convalescence, the rabbits were subjected to the experiment described below. After the experiment, methylene blue was injected to verify the cannula placement.

iii) Antinociception test

The rabbits were retained with a rabbit retainer and a hole having a diameter of 1 mm and a depth 1 mm was bored into both lateral sides of an upper major incisor with a dentist's drill. A stimulating electrode was fitted into each hole and electric stimulation (5 msec, 5 Hz, 3 sec duration) was applied at various voltages from an electric stimulator (Nihon Kohden Corp.) to measure the stimulation threshold values (V) that induced licking responses (licking and the movement of lips and lower jaw) in the animals. Measurements were conducted one hour before drug administration and, immediately after the administration, as well as 0.5 h, 1.0 h, 1.5 h, 2.0 h, 3.0 h and 4.0 h after the administration.

The drugs tested were (1–16) human/(17–32) salmon hybrid calcitonin (hybrid calcitonin 1), salmon calcitonin and human calcitonin, each of which was administered intraventricularly in an amount equivalent to 8 IU/kg. Physiological saline was used as a control.

Results and Discussion

Figure 2:
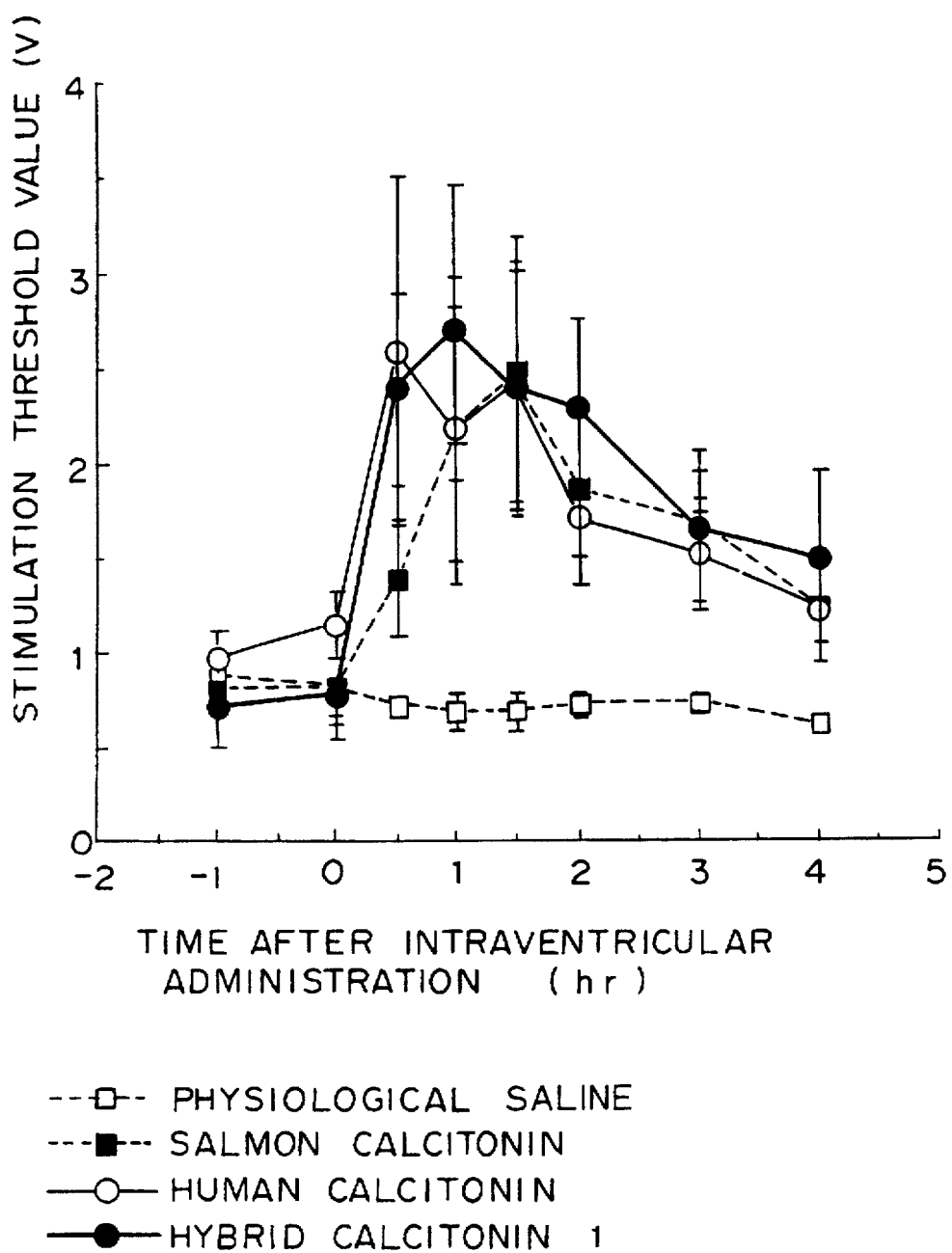
FIG. 2 is a graph showing the time-dependent profile of stimulation threshold values following administration of various types of calcitonin.

The time-dependent profiles of stimulation threshold for the test calcitonins are shown in FIG. 2. As one can see from FIG. 2, the three calcitonins caused comparable increases in threshold value that peaked 0.5–1.5 h after drug administration. It is therefore calculated that the hybrid calcitonin of the present invention is as effective as salmon calcitonin and human calcitonin in analgesic action.

EXAMPLE 11

Effects of calcitonins on the inhibition of body weight gain and appetite

Method

Rats were injected intramuscularly with (1–16) human/(17–32) salmon hybrid calcitonin (hybrid calcitonin 1), human calcitonin and elcatonin, and their body weight and food consumptions were measured 24 h later.

Results

Figure 3:
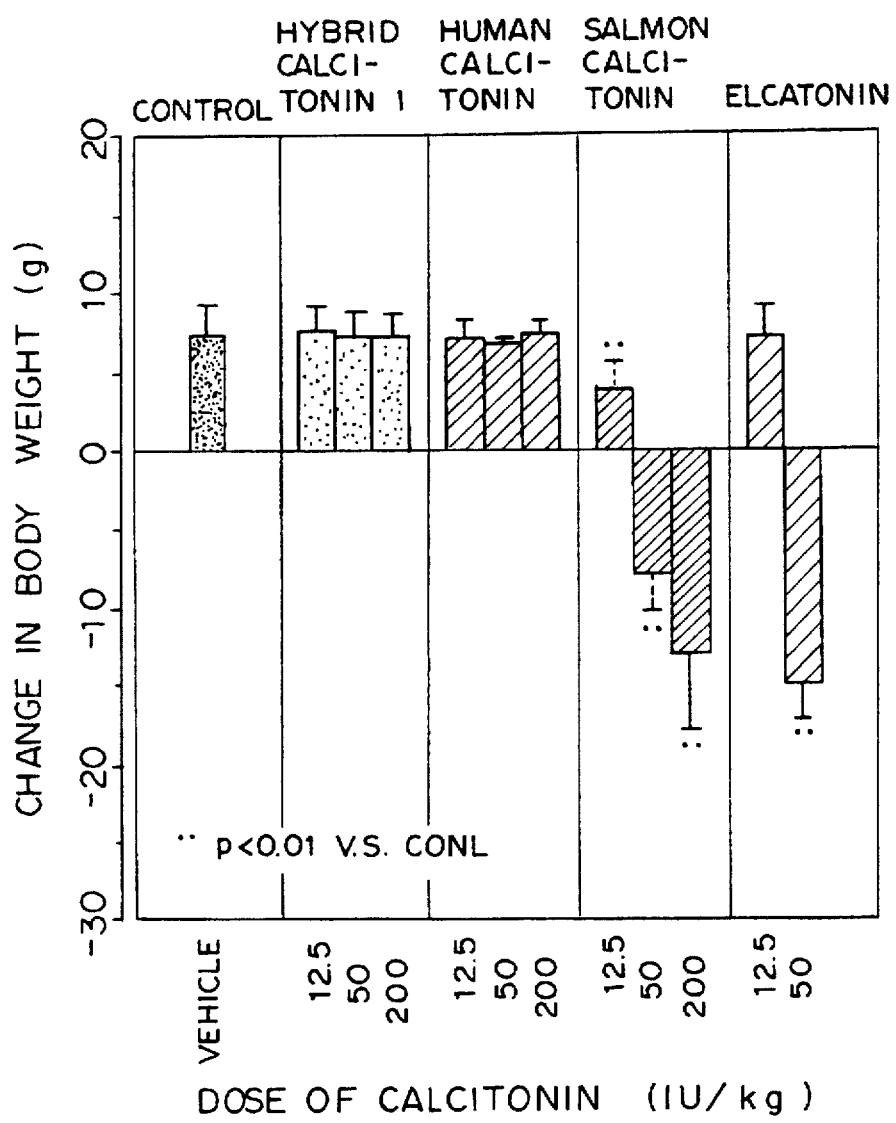
FIG. 3 is a graph showing the changes in the body weight of rats administered various types of calcitonin.
Figure 4:
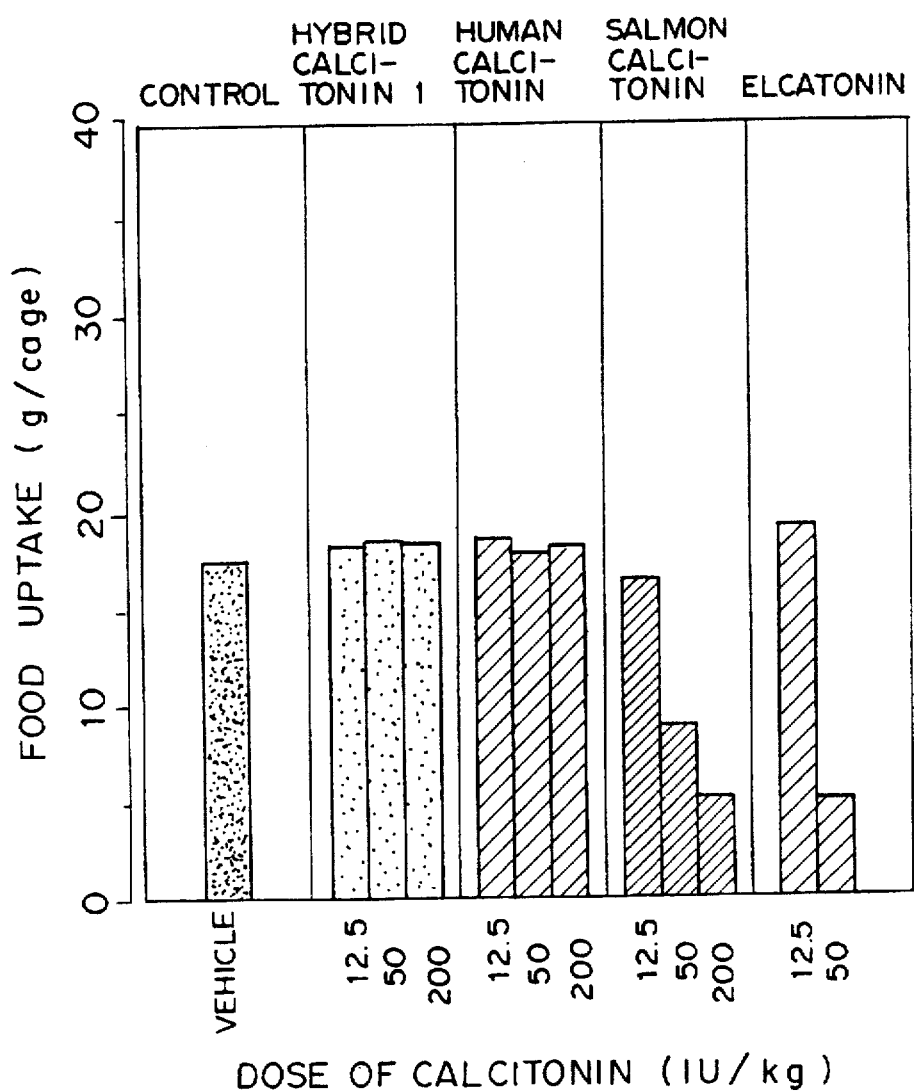
FIG. 4 is a graph showing the food uptakes of the rats administered various types of calcitonin.

The changes in the body weight of rats administered various calcitonins are shown in FIG. 3, and their food consumptions in FIG. 4. Each of the calcitonins was administered in three different doses: 12.5 IU/kg, 50 IU/kg and 200 IU/kg. For the body weight changes, the measured values were averaged for 5 rats, and for the food consumption, the measured values for 5 rats were added together.

Discussion

As is clear from FIGS. 3 and 4, salmon calcitonin and elcatonin exhibited dose-dependent effects on the inhibition of body weight gain and appetite, whereas hybrid calcitonin 1 and human calcitonin caused no differences in body weight and food consumption. It can therefore be concluded that the hybrid calcitonin of the present invention causes as little effects on body weight gain and appetite as human calcitonin.

EXAMPLE 12

Effects of calcitonins on gastric emptying time

Method

Female beagles fasted from the previous day were injected with (1–16) human/(17–32) salmon hybrid calcitonin (hybrid calcitonin 1), salmon calcitonin, human calcitonin and physiological saline through one cephalic vein. One hour later, enteric aspirin tablets (containing 200 mg of the active ingredient) were administered orally together with 25 ml of water. Thereafter, blood samples were taken from the other cephalic vein at given time intervals, and the plasma obtained in the usual manner was stored at −20° C. until measurement.

As it passes through the intestinal wall, most of the ingested aspirin is metabolized and enters the blood stream as salicylic acid. Hence, salicylic acid in plasma was determined as a marker for aspirin. Ethanol (200 μl) was added to 50 μl of plasma and the mixture was centrifuged at 10,000 rpm×1 min, with the resulting supernatant being subjected to HPLC.

Results

The delaying action of each calcitonin on the gastric emptying time is summarized in Table 9. The difference between the time from calcitonin administration to the absorption of aspirin and the time from physiological saline administration to the absorption of aspirin was calculated for each animal to determine the delay in gastric emptying time.

TABLE 9

| Calcitonin | Dose, μg (IU)/kg | Lag time, h | | | Delay time, h | | |
|---|---|---|---|---|---|---|---|
| Hybrid calcitonin 1 | 0.6 (1.2) | 1.9 | 4.8 | 7.7 | 0.0 | 3.2 | 6.6 |
| | 10 (21.0) | 5.1 | 18.0 | 21.4 | 3.8 | 16.3 | 20.3 |
| Salmon calcitonin | 0.1 (0.4) | 2.0 | 2.0 | | 0.3 | 0.7 | |
| | 0.3 (1.2) | 2.7 | 4.5 | 11.1 | 0.0 | 3.9 | 10.0 |
| | 0.6 (2.4) | 22.0 | 30.0 | 45.0 | 19.4 | 29.4 | 43.1 |
| Human calcitonin | 6 (1.2) | 3.0 | 3.9 | 4.0 | 1.3 | 2.6 | 2.9 |
| | 100 (20.0) | 5.0 | 6.9 | | 4.4 | 5.0 | |

Notes Lag time: time from aspirin administration to its absorption
Delay time: difference in time to aspirin absorption between calcitonin and physiological saline Discussion As Table 9 shows, salmon calcitonin had a very strong action in delaying the gastric emptying time, whereas human calcitonin was weak in such action. Hybrid calcitonin 1 was more similar to human calcitonin than salmon calcitonin in delaying to gastric emptying time. It can therefore be concluded that the hybrid calcitonin 1 of the present invention can be administered in a higher dose of activity units than salmon calcitonin.

EXAMPLE 13

Effects of calcitonins on gastrointestinal motility in conscious dog.

Method

A healthy beagle dog weighing about 10 kg was anesthetized with an i.v. injection of pentobarbital sodium and the abdominal cavity was opened under aseptic conditions.

Extraluminal force transducers were sutured onto the serosa of the gastric antrum stomach, duodenum and jejunum to measure circular muscle contraction, as reported previously (Itoh et al. Gastroenterol Jpn. 12, 275 1977).

The lead wires of these transducers were out of the abdominal cavity and then brought out through a skin incision made between the scapulae.

After the abdominal surgery, a 5-cm longitudinal skin incision was made in the right Frontal neck to expose the external jugular vein.

A Silastic tube (French size 8.5, Dow corning, Midland, Mich.) was placed into the superior vena cava through the vein and sutured onto the adjacent skin as a route for the i.v. injection of test drugs.

After the operation, a jacket protector was placed on the dog to protect the lead wires and the Silastic tube.

The dog was housed in individual experimental cage, and given commercial dog food at 5:00 P.M. and water was given freely.

The gastrointestinal motor activity was recorded on a thermal pen writing recorder (WR-3101, Graphtic, Tokyo, Japan) by connecting the lead wires of the transducers to the connecting cables from the amplifiers (UG-5, Nihon Kohden, Tokyo, Japan).

About two weeks postoperation, gastrointestinal contractile activity could be divided into two main patterns of activity, the interdigestive and digestive states.

In the interdigestive state, IMC (interdigestive migrating motor complex) were seen to occur at regular intervals of 100 to 120 min. in the gastric antrum, and migrated through the duodenum and jejunum at a constant velocity.

In all animals, feeding disrupted the regular IMC pattern. Experiments were carried out during interdigestive state. The drug was dissolved into 0.9% saline and administered through the indwelling Silastic tube for about 10 seconds in a volume of 0.3 ml/kg.

15 Min after the end of the IMC in the gastric antrum, which were subsequently flushed in with 0.9% saline.

The time until the next IMC is occurred from administration of the drug was measured, and used as a index for inhibitory activity of the drug on gastrointestinal motility.

The results are shown in Table 10.

Results

TABLE 10

| | | | | | | |
|---|---|---|---|---|---|---|
| Salmon calcitonin | Dose, µg/kg | 0.1 | 0.3 | 1.0 | 3 | |
| | (U/kg) | (0.4) | (1.2) | (4.0) | (12) | |
| | IMC delay | 0 | 1 | 2 | 3 | |
| Human calcitonin | Dose, µg/kg | 100 | 300 | 1000 | | |
| | (U/kg) | (20) | (60) | (200) | | |
| | IMC delay | 0 | 0.5 | 0.5 | | |
| Hybrid calcitonin 1 | Dose, µg/kg | 0.03 | 0.1 | 1.0 | 3.0 | 100 |
| | (U/kg) | (0.06) | (0.21) | (2.1) | (6.3) | (210) |
| | IMC delay | 0 | 0.5 | 1 | 1 | 1 |
| Hybrid calcitonin 2 | Dose, µg/kg | 0.3 | 1.0 | 3.0 | 10 | 30 | 100 |
| | (U/kg) | (0.5) | (1.8) | (5.4) | (18) | (54) | (180) |
| | IMC delay | 0 | 0.5 | 1 | 1 | 1 | 1 |

Notes: 1. The indexes of "IMC delay" mean as follows.
0 ... Next IMC occurred within 180 min after administration.
0.5 ... Next IMC occurred more than 180 min but within 300 min after administration.
1 ... Next IMC occurred one day after administration.
2 ... Next IMC occurred two days after administration.
3 ... Next IMC occurred three days after administration.
2. Hybrid calcitonin 1 as (1–16) human/(17–32) salmon calcitonin, and hybrid calcitonin 2 was (1–21) human/(22–32) salmon calcitonin.

Discussion

As reported in Table 10, salmon calcitonin administered i.v. does-dependently inhibited the occurrence of the next IMC in conscious dog.

At a dose of 3 µg/kg, it delayed the occurrence of the next IMC 3 days. On the other hand, human calitonin had only a slight effect on the IMC.

Although hybrid calcitonins also inhibited the IMC, these compounds delayed the occurrence of the next IMC only one day even at the highest dosage examined (100 µg/kg).

Our results definitely demonstrate that hybrid calcitonins had a weaker effect on gastrointestinal motility in conscious dogs than salmon calcitonin.

These results also indicated that hybrid calcitonins will probably cause less adverse effects on gastrointestinal tract than salmon calcitonin.

EXAMPLE 14

Cross reaction between anti-salmon calcitonin human antibody and hybrid calcitonin.

Method

Salmon calcitonin was synthesized by an ordinary procedure of solid-phase synthesis. Salmon calcitonin labelled with $^{125}I$ was prepared by the Tejedor method (Tejedor, F. and Ballesta, J. P. G.; Analytical Biochemistry, 127, 143–149 (1982)).

Four types of human sera that had been verified to contain antibody after administration of salmon calcitonin were furnished from Dr. Frederick R. Singer (CEDERS-SINAI MEDICAL CENTER). The antibody titres of those sera against salmon calcitonin were as follows:

| No. 1 | 1:4000 | No. 2 | 1:8000 |
|---|---|---|---|
| No. 3 | 1:8000 | No. 4 | 1:2000 |

1) Determining the ratio of serum dilution

A 0.1M borate buffer solution (pH 8.0) containing 0.5% BSA, 0.9% NaCl, 0.1% $NaN_3$ and 0.05% Tween 20 was used as a reaction buffer. This reaction buffer, anti-salmon calcitonin human serum (diluted with the reaction buffer to a final dilution of 100–6,400) and a solution of labelled calcitonin were charged into an assist tube (Spitz type of Salschted Inc. measuring 12×75 mm) in the respective volumes shown below, stirred thoroughly, and left to stand overnight at room temperature.

| | | *1 | *2 |
|---|---|---|---|
| i) | Reaction buffer | 300 µl | 400 µl |
| ii) | Anti-salmon calcitonin human serum | 100 µl | 0 µl |
| iii) | Solution of labelled calcitonin (≃ 20,000 cpm) | 100 µl | 100 µl |

*1 Total binding (B)
*2 Non-specific binding (NSB)

Figure 5:
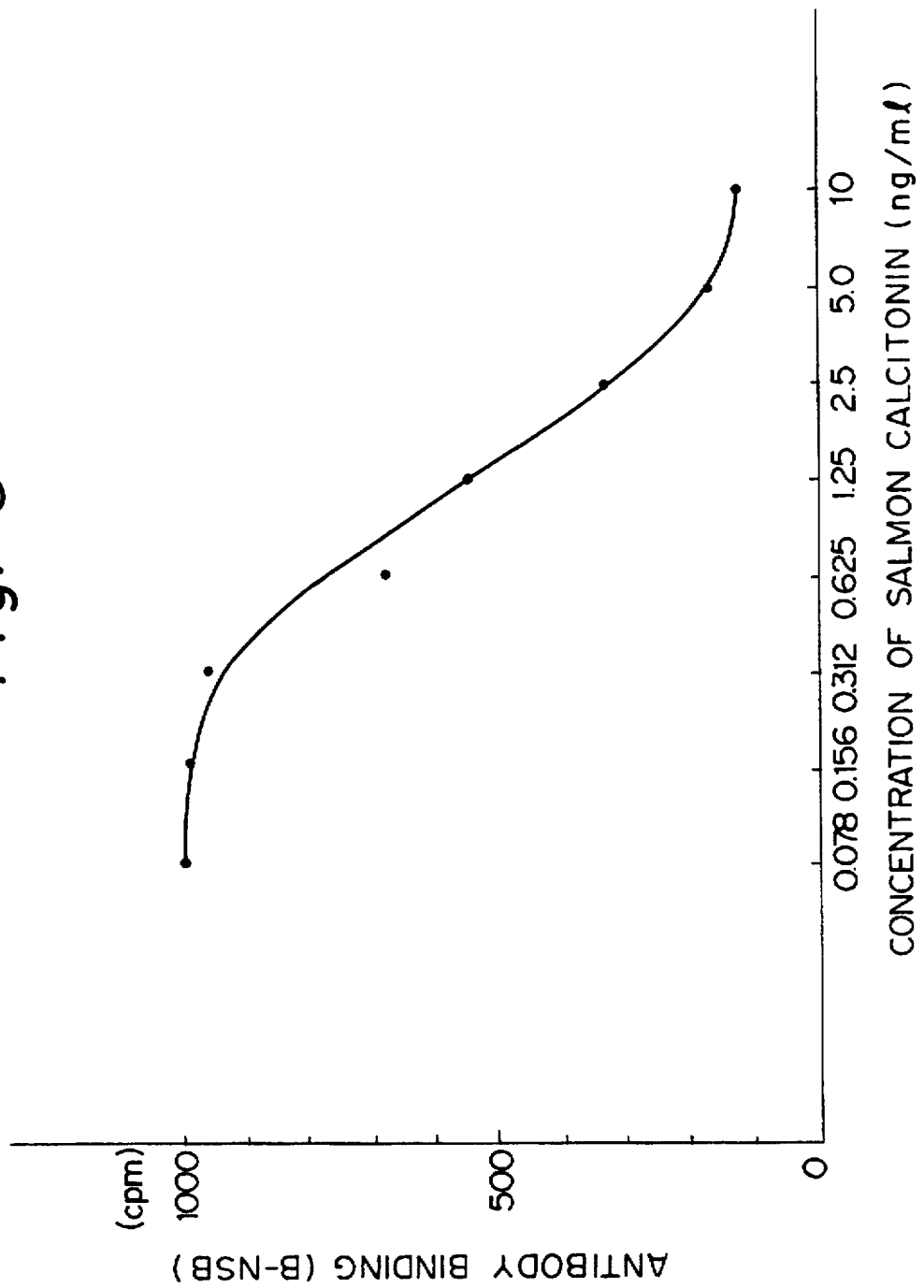
FIG. 5 is a graph showing the relationship between the concentration of salmon calcitonin and antibody binding.
Figure 6:
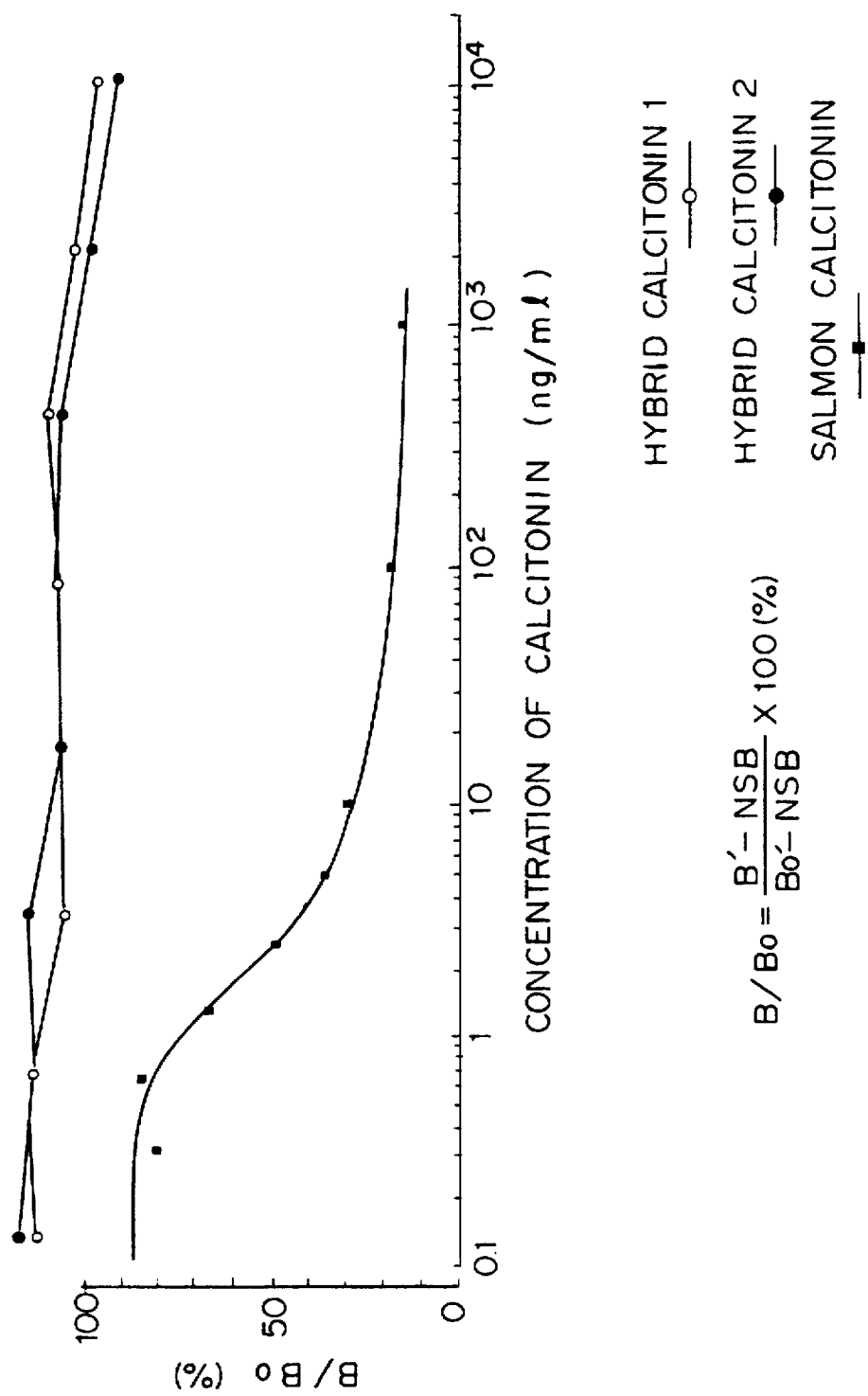

The reaction solution was mixed well with 500 µl of 0.2% BGG (bovine γ-globulin, Sigma), further mixed with 1 ml of 25% PEG #6000, stirred thoroughly and thereafter left to stand at room temperature for 15 min. The reaction solution was then centrifuged with a bucket type centrifuge (05RP-22 of Hitachi) at 3,000 rpm for 10 min at 4° C. After removing the supernatant by aspiration, the radioactivity level of the residue was measured with a gamma-counter. The results are shown in FIG. 5.

2) Reaction of competition between $^{125}I$ labelled salmon calcitonin and salmon calcitonin or hybrid calcitonin The reaction buffer, various types of calcitonin, anti-salmon calcitonin human serum and the solution of labelled calcitonin were charged into an assist tube in the respective volumes indicated below and subsequently treated in the same way as in the determination of serum dilution.

| | | *1 | *2 | *3 |
|---|---|---|---|---|
| i) | Reaction buffer | 200 µl | 400 µl | 300 µl |
| ii) | calcitonin | 100 µl | 0 µl | 0 µl |
| iii) | Anti-salmon calcitonin human serum | 100 µl | 0 µl | 100 µl |
| iv) | Solution of labelled calcitonin (≃ 20,000 cpm) | 100 µl (B') | 100 µl (NSB) | 100 µl (Bo') |

The two hybrid calcitonins used were: 1. (1–16) human/(17–32) salmon calcitonin; 2. (1–21) human/(22–32) salmon calcitonin.

The results are shown in FIGS. 6–9.

Results and Discussion

Investigation was made as to whether $^{125}I$ labelled salmon calcitonin would compete with salmon calcitonin for anti-salmon calcitonin human serum No. 1 (FIG. 5). Similar curves were obtained when anti-salmon calcitonin human sera Nos. 2–4 were used. These results indicate that salmon calcitonin started to compete with the labelled salmon calcitonin in a dose of at least 1 ng/ml.

Experiments with the four types of sera demonstrated that neither hybrid calcitonin 1 nor 2 was recognized by the anti-salmon calcitonin human sera (FIGS. 6–9).

It is therefore concluded that the hybrid calcitonin of the present invention can potentially be used as an effective drug for patients who produce anti-salmon calcitonin antibodies.

The hybrid calcitonin of the present invention has the outstanding advantage that it exhibits as strong biological activities as salmon, eel and chicken calcitonins while causing no side effects including nausea, disorders in the functions of the digestive tract and antigenicity. It also has a process advantage in that side reactions that would otherwise be encountered during synthesis can be prevented by changing $Met^8$ in human calcitonin to $Val^8$.

What is claimed is:

1. A hybrid calcitonin molecule consisting of an amino acid sequence SEQ ID NO:3.

2. The hybrid calcitonin molecule according to claim 1, consisting of the amino acid sequence of SEQ ID NO:4.

3. The hybrid calcitonin molecule according to claim 1, consisting of the amino acid sequence of SEQ ID NO:5.

4. The hybrid calcitonin molecule according to claim 1, consisting of the amino acid sequence of SEQ ID NO:6.

5. The hybrid calcitonin molecule according to claim 1, consisting of the amino acid sequence of SEQ ID NO:7.

6. The hybrid calcitonin molecule according to claim 1, consisting of the amino acid sequence of SEQ ID NO:8.

7. The hybrid calcitonin molecule according to claim 1, consisting of the amino acid sequence of SEQ ID NO:9.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( B ) LOCATION: 32
        ( D ) OTHER INFORMATION: /note= Pro = prolinamide ( x i ) SEQUENCE DESCRIPTION: SEQ ID NO:1:

```
Cys Gly Asn Leu Ser Thr Cys Met Leu Gly Thr Tyr Thr Gln Asp Phe
 1               5                  10                  15

Asn Lys Phe His Thr Phe Pro Gln Thr Ala Ile Gly Val Gly Ala Pro
                20                  25                  30
```

( 2 ) INFORMATION FOR SEQ ID NO:2:

( i ) SEQUENCE CHARACTERISTICS:
  ( A ) LENGTH: 32 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( B ) LOCATION: 32
  ( D ) OTHER INFORMATION: /note= Pro = prolinamide ( x i ) SEQUENCE DESCRIPTION: SEQ ID NO:2:

```
Cys Ser Asn Leu Ser Thr Cys Val Leu Gly Lys Leu Ser Gln Glu Leu
1               5                   10                  15

His Lys Leu Gln Thr Tyr Pro Arg Thr Asp Val Gly Ala Gly Thr Pro
            20                  25                  30
```

( 2 ) INFORMATION FOR SEQ ID NO:3:

( i ) SEQUENCE CHARACTERISTICS:
  ( A ) LENGTH: 32 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Active-site
  ( B ) LOCATION: 8
  ( D ) OTHER INFORMATION: /note= "This amino acid can be either Met or Val"

( i x ) FEATURE:
  ( A ) NAME/KEY: Active-site
  ( B ) LOCATION: 15
  ( D ) OTHER INFORMATION: /note= "This amino acid can be either Asp or Glu"

( i x ) FEATURE:
  ( A ) NAME/KEY: Active-site
  ( B ) LOCATION: 16
  ( D ) OTHER INFORMATION: /note= "This amino acid can be either Phe or Leu"

( i x ) FEATURE:
  ( A ) NAME/KEY: Active-site
  ( B ) LOCATION: 17
  ( D ) OTHER INFORMATION: /note= "This amino acid can be either Asn or His"

( i x ) FEATURE:
  ( A ) NAME/KEY: Active-site
  ( B ) LOCATION: 19
  ( D ) OTHER INFORMATION: /note= "This amino acid can be either Phe or Leu or Des"

( i x ) FEATURE:
  ( A ) NAME/KEY: Active-site
  ( B ) LOCATION: 20
  ( D ) OTHER INFORMATION: /note= "This amino acid can be either His or Gln"

( i x ) FEATURE:
  ( A ) NAME/KEY: Active-site
  ( B ) LOCATION: 27
  ( D ) OTHER INFORMATION: /note= "This amino acid can be either Thr or Val"

( i x ) FEATURE:
  ( A ) NAME/KEY: Active-site
  ( B ) LOCATION: 29
  ( D ) OTHER INFORMATION: /note= "This amino acid can be either Ser or Ala"

(i x) FEATURE:
    (B) LOCATION: 32
    (D) OTHER INFORMATION: /note= Pro = prolinamide (x i) SEQUENCE DESCRIPTION: SEQ ID NO:3:

```
Cys Gly Asn Leu Ser Thr Cys Xaa Leu Gly Thr Tyr Thr Gln Xaa Xaa
1               5                   10                  15
Xaa Lys Xaa Xaa Thr Tyr Pro Arg Thr Asx Xaa Gly Xaa Gly Thr Pro
            20                  25                  30
```

(2) INFORMATION FOR SEQ ID NO:4:

(i) SEQUENCE CHARACTERISTICS:
    (A) LENGTH: 32 amino acids
    (B) TYPE: amino acid
    (C) STRANDEDNESS: single
    (D) TOPOLOGY: linear (i i) MOLECULE TYPE: peptide (i x) FEATURE:
    (B) LOCATION: 32
    (D) OTHER INFORMATION: /note= Pro = prolinamide (x i) SEQUENCE DESCRIPTION: SEQ ID NO:4:

```
Cys Gly Asn Leu Ser Thr Cys Met Leu Gly Thr Tyr Thr Gln Asp Phe
1               5                   10                  15
His Lys Leu Gln Thr Tyr Pro Arg Thr Asn Thr Gly Ser Gly Thr Pro
            20                  25                  30
```

(2) INFORMATION FOR SEQ ID NO:5:

(i) SEQUENCE CHARACTERISTICS:
    (A) LENGTH: 32 amino acids
    (B) TYPE: amino acid
    (C) STRANDEDNESS: single
    (D) TOPOLOGY: linear (i i) MOLECULE TYPE: peptide (i x) FEATURE:
    (B) LOCATION: 32
    (D) OTHER INFORMATION: /note= Pro = prolinamide (x i) SEQUENCE DESCRIPTION: SEQ ID NO:5:

```
Cys Gly Asn Leu Ser Thr Cys Met Leu Gly Thr Tyr Thr Gln Asp Phe
1               5                   10                  15
His Lys Leu Gln Thr Tyr Pro Arg Thr Asp Val Gly Ala Gly Thr Pro
            20                  25                  30
```

(2) INFORMATION FOR SEQ ID NO:6:

(i) SEQUENCE CHARACTERISTICS:
    (A) LENGTH: 32 amino acids
    (B) TYPE: amino acid
    (C) STRANDEDNESS: single
    (D) TOPOLOGY: linear (i i) MOLECULE TYPE: peptide (i x) FEATURE:
    (B) LOCATION: 32
    (D) OTHER INFORMATION: /note= Pro = prolinamide (x i) SEQUENCE DESCRIPTION: SEQ ID NO:6:

```
Cys Gly Asn Leu Ser Thr Cys Val Leu Gly Thr Tyr Thr Gln Asp Phe
1               5                   10                  15
His Lys Leu Gln Thr Tyr Pro Arg Thr Asp Val Gly Ala Gly Thr Pro
            20                  25                  30
```

( 2 ) INFORMATION FOR SEQ ID NO:7:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( B ) LOCATION: 31
        ( D ) OTHER INFORMATION: /note= Pro = prolinamide ( x i ) SEQUENCE DESCRIPTION: SEQ ID NO:7:

```
Cys Gly Asn Leu Ser Thr Cys Met Leu Gly Thr Tyr Thr Gln Asp Phe
 1               5                  10                  15
His Lys Gln Thr Tyr Pro Arg Thr Asp Val Gly Ala Gly Thr Pro
            20                  25                  30
```

( 2 ) INFORMATION FOR SEQ ID NO:8:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( B ) LOCATION: 32
        ( D ) OTHER INFORMATION: /note= Pro = prolinamide ( x i ) SEQUENCE DESCRIPTION: SEQ ID NO:8:

```
Cys Gly Asn Leu Ser Thr Cys Met Leu Gly Thr Tyr Thr Gln Glu Leu
 1               5                  10                  15
His Lys Leu Gln Thr Tyr Pro Arg Thr Asn Thr Gly Ser Gly Thr Pro
            20                  25                  30
```

( 2 ) INFORMATION FOR SEQ ID NO:9:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( B ) LOCATION: 32
        ( D ) OTHER INFORMATION: /note= Pro = prolinamide ( x i ) SEQUENCE DESCRIPTION: SEQ ID NO:9:

```
Cys Gly Asn Leu Ser Thr Cys Met Leu Gly Thr Tyr Thr Gln Asp Phe
 1               5                  10                  15
Asn Lys Phe His Thr Tyr Pro Arg Thr Asn Thr Gly Ser Gly Thr Pro
            20                  25                  30
```

( 2 ) INFORMATION FOR SEQ ID NO:10:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Active-site
    ( B ) LOCATION: 11
    ( D ) OTHER INFORMATION: /note= "This amino acid can be either Thr or Lys"

( i x ) FEATURE:
    ( A ) NAME/KEY: Active-site
    ( B ) LOCATION: 12
    ( D ) OTHER INFORMATION: /note= "This amino acid can be either Tyr or Leu"

( i x ) FEATURE:
    ( A ) NAME/KEY: Active-site
    ( B ) LOCATION: 13
    ( D ) OTHER INFORMATION: /note= "This amino acid can be either Thr or Ser"

( i x ) FEATURE:
    ( A ) NAME/KEY: Active-site
    ( B ) LOCATION: 15
    ( D ) OTHER INFORMATION: /note= "This amino acid can be either Asp or Glu"

( i x ) FEATURE:
    ( A ) NAME/KEY: Active-site
    ( B ) LOCATION: 16
    ( D ) OTHER INFORMATION: /note= "This amino acid can be either Phe or Leu"

( i x ) FEATURE:
    ( A ) NAME/KEY: Active-site
    ( B ) LOCATION: 17
    ( D ) OTHER INFORMATION: /note= "This amino acid can be either Asn or His"

( i x ) FEATURE:
    ( A ) NAME/KEY: Active-site
    ( B ) LOCATION: 19
    ( D ) OTHER INFORMATION: /note= "This amino acid can be either Phe or Leu or des"

( i x ) FEATURE:
    ( A ) NAME/KEY: Active-site
    ( B ) LOCATION: 20
    ( D ) OTHER INFORMATION: /note= "This amino acid can be either His or Gln"

( i x ) FEATURE:
    ( A ) NAME/KEY: Active-site
    ( B ) LOCATION: 26
    ( D ) OTHER INFORMATION: /note= "This amino acid can be either Asn or Asp"

( i x ) FEATURE:
    ( A ) NAME/KEY: Active-site
    ( B ) LOCATION: 27
    ( D ) OTHER INFORMATION: /note= "This amino acid can be either Val or Thr"

( i x ) FEATURE:
    ( A ) NAME/KEY: Active-site
    ( B ) LOCATION: 29
    ( D ) OTHER INFORMATION: /note= "This amino acid can be either Ala or Ser"

( i x ) FEATURE:
    ( B ) LOCATION: 32
    ( D ) OTHER INFORMATION: /note= Pro = prolinamide ( x i ) SEQUENCE DESCRIPTION: SEQ ID NO:10:

```
Cys Gly Asn Leu Ser Thr Cys Xaa Leu Gly Xaa Xaa Xaa Gln Xaa Xaa
 1               5                  10                  15
Xaa Lys Xaa Xaa Thr Tyr Pro Arg Thr Xaa Xaa Gly Xaa Gly Thr Pro
             20                  25                  30
```